United States Patent
Bennett-Guerrero et al.

(10) Patent No.: US 6,749,831 B1
(45) Date of Patent: Jun. 15, 2004

(54) VACCINE AGAINST LIPOPOLYSACCHARIDE CORE

(75) Inventors: Elliott Bennett-Guerrero, New York, NY (US); George Robin Barclay, Midlothian (GB); Ian Raymond Poxton, Edinburgh (GB); Thomas James McIntosh, Durham, NC (US); David Scott Snyder, Durham, NC (US)

(73) Assignee: Medical Defense Technology, LLC, New York, NY (US)

(*) Notice: Subject to any disclaimer, the term of this patent is extended or adjusted under 35 U.S.C. 154(b) by 0 days.

(21) Appl. No.: 09/423,546

(22) PCT Filed: May 15, 1998

(86) PCT No.: PCT/US98/09988

§ 371 (c)(1),
(2), (4) Date: Apr. 25, 2000

(87) PCT Pub. No.: WO98/51217

PCT Pub. Date: Nov. 19, 1998

Related U.S. Application Data

(60) Provisional application No. 60/046,680, filed on May 16, 1997.

(51) Int. Cl.[7] .................. A61K 51/00; A61K 39/40; A61B 5/055
(52) U.S. Cl. ............... 424/1.21; 424/9.321; 424/169.1; 424/236.1; 424/241.1; 424/258.1; 427/2.14; 530/390.1
(58) Field of Search .................. 424/1.21, 9.321, 424/169.1, 236.1, 241.1, 258.1; 427/2.14; 530/390.1

(56) References Cited

U.S. PATENT DOCUMENTS

| | | |
|---|---|---|
| 4,053,585 A | 10/1977 | Allison et al. |
| 4,199,565 A | 4/1980 | Fullerton |
| 4,235,871 A | 11/1980 | Papahadjopoulos |
| 4,235,877 A | 11/1980 | Fullerton |
| 4,241,046 A | 12/1980 | Papahadjopoulos |
| 4,285,936 A | 8/1981 | Pier et al. |
| 4,416,872 A | 11/1983 | Alving et al. ............. 424/177 |
| 4,693,891 A | 9/1987 | Collins et al. |
| 4,755,381 A | 7/1988 | Cryz |
| 4,755,382 A | 7/1988 | Flaherty |
| 4,771,127 A | 9/1988 | Cryz et al. |
| 4,777,136 A | 10/1988 | Young |
| 4,789,544 A | 12/1988 | Nelson et al. ............. 424/92 |
| 4,844,894 A | 7/1989 | Ribi |
| 4,946,677 A | 8/1990 | Dorner et al. |
| 5,026,557 A | 6/1991 | Estis et al. |
| 5,057,598 A | 10/1991 | Pollack et al. |
| 5,059,591 A | 10/1991 | Janoff et al. |
| 5,114,712 A | 5/1992 | Fukuda et al. |
| 5,179,018 A | 1/1993 | Bogard, Jr. et al. |
| 5,370,872 A | 12/1994 | Cryz et al. |
| 5,417,986 A | 5/1995 | Reid et al. |
| 5,426,046 A | 6/1995 | Kaplan et al. |
| 5,730,989 A | 3/1998 | Wright |
| 5,750,115 A | 5/1998 | Van Den Bosch |
| 5,858,728 A * | 1/1999 | Gram et al. ............. 435/70.21 |

FOREIGN PATENT DOCUMENTS

| | | | |
|---|---|---|---|
| WO | WO 87/07148 | 12/1987 | ......... A61K/39/116 |
| WO | WO90/03186 | 4/1990 | |
| WO | WO91/15239 | 10/1991 | |
| WO | WO 92/06709 | 4/1992 | ......... A61K/39/02 |
| WO | WO 92/16624 | 10/1992 | ......... C12N/15/13 |
| WO | WO92/20370 | 11/1992 | |
| WO | WO93/08834 | 5/1993 | |
| WO | WO 93/10216 | 5/1993 | ......... C12N/1/36 |
| WO | WO 95/29662 | 11/1995 | |
| WO | WO 96/25146 | 8/1996 | |

OTHER PUBLICATIONS

Johns et al, Immunization with R mutants of *Salmonella minnesota*. II. Serological response to Lipid A and the lipopolysaccharide of Re mutants. Infection and Immunity, vol. 17, No. 1, pp. 9–15, 1977.*

Adhikari et al., "Septicaemic low birthweight neonates treated with human antibodies to endotoxin", Archives of Disease in Childhood, (1985) 382–384.

Allan, Elizabeth et al., "Antibacteroides lipopolysaccharide IgG levels in healthy adults and sepsis patients", FEMS Immunology and Medical Microbiology 11 (1995) 5–12.

Alving, Carl R., "Lipid A and Liposomes Containing Lipid A As Adjuvants for Vaccines", vol. II: Immunopharmacology and Pathophysiology, Ch. 18, 429–438.

Alving, Carl R., "Macrophages as targets for delivery of liposome–encapsulated entimicrobial agents", Advanced Drug Delivery Reviews, 2 (1988) 107–128.

Alving, Carl R., "Delivery of Liposome–Encapsulated Drugs to Macrophages", Pharmac. Ther. vol. 22 (1983) pp. 407–424.

Alving, Carl R., "Lipopolysaccharide, Lipid A, and Liposomes Containing Lipid A as Immunologic Adjuvants", Immunogiol. vol. 187 (1993) 430–446.

Alving, Carl R. et al., "Adjuvanticity of Lipid A and Lipid A Fractions in Liposomes", Elsevier North Holand, Inc, (1980) 67–78.

Alving, Carl R., "Immunologic aspects of liposomes: presentation and processing of liposomal protein and phospholipid antigens", Biochimica et Biophysica Acta, 1113 (1992) 307–322.

(List continued on next page.)

Primary Examiner—Rodney P. Swartz
(74) Attorney, Agent, or Firm—Fish & Richardson, P.C.

(57) ABSTRACT

Compare core LPS (lacking O-polysaccharide side chains) from Gram-negative bacteria are incorporated into a vaccine typically in liposomes. The complete core of *E. coli* K 12 is particularly useful. Upon administration to a mammal the vaccine stimulates synthesis of antibodies which are cross-protective against smooth and rough forms of LPS from at least two different Gram-negative bacterial strains having different core structures.

32 Claims, 3 Drawing Sheets

OTHER PUBLICATIONS

Alving, Carl R., "Liposomes as carriers of antigens and adjuvants", Journal of Immunological Methods, 140 (1991) 1–13.

Alving, Carl R., "Liposomes as Carriers for Vaccines", Walter Reed Army Institute of Research, Washington, DC, Ch. 6 195–218.

Alving, Carl R., "Liposomes containing lipid A: a porent nontoxic adjuvant for a human malaria sporozoite vaccine", Immunology Letters, 25 (1990) 275–280.

Appelmelk, B.J. et al., "Recombinant Human Bactericidal/Permeability–Increasing Protein (rBPI23) Is a Universal Lipopolysaccharide–Binding Ligand", Injection and Immunity (1994) 3564–3567.

Appelmelk, B.J. et al., "Antigenic and immunogenic differences in lipopolysaccharides of *Escherchia coli* J5 vaccine strains of different origins", Jour of General Microbiology (1993) 3641–2647.

Ashton, F.E. et al., "Short communication—Protective efficacy of mouse serum to the N–propionyl derivative of meningococcal group B polysaccharide", Microbial Pathogenesis (1989) 455–458.

Astiz, Mark E. et al., "Pretreatment of normal humans with monophosphoryl lipid A induces tolerance to endotoxin: A prospective double–blind, randomized, controlled trial", Critical Care Medicine, vol. 23, No. 1 (1995) 9–17.

Baker, Phillip J. et al., "Structural Features that Influence the Ability of Lipid A and Its Analogs to Abolish Expression of Suppressor T Cell Activity", Infection and Immunity, Jul. 1992, 2694–2701.

Baker, Phillip J. et al., "Ability of Monophosphoryl Lipid A to Augment the Antibody Response of Young Mice", Infection and Immunity, Dec. 1988, 3064–3066.

Bakouche, Ouahid et al., "Interleukin 1 Release by Human Monocytes Treated with Liposome–Encapsulated Lipopolysaccharide", Journal of Immunology, vol. 139 (1987) 1120–1126.

Barclay, G.R. et al., "Serological Relationships between *Escherichia coli* and Salmonella Smooth–and Rough–Mutant Lipopolysaccharides as Revealed by Enzyme–Linked Immunosorbent Assay for Human Immunoglobulin G Antiendotoxin Antibodies", Infection and Immunity (1987) 2706–2714.

Battafarano, Richard J. et al., "Peptide derivatives of three distinct lipopolysaccharide binding proteins inhibit lipopolysaccharide–induced tumor necrosis factor–alpha secretion in vitro", Surgery (1995) 318–324.

Baumgartner, Jean–Daniel, "Immunotherapy with Antibodies to Core Lipopolysaccharide: A Critical Appraisal", Infection Disease of North American, vol. 5, No. 4 (1991) 915–927.

Baumgartner, Jean Daniel et al., "Prevention of Gram–Negative Shock and Death in Surgical Patients by Antibody to Endotoxin Core Glycolipid", The Lancet Ltd. (1985) 59–63.

Baumgartner, J.D. et al., "Interpretation of Data Regarding the Protection Afforded by Serum, IgG, or IgM Antibodies after Immunization with the Rough Mutant R595", Journal of Infectious Diseases, vol. 160, No. 2 (1989) 347–349.

Baumgartner, Jean–Daniel et al., "Immunotherapy of Endotoxemia and Septicemia", Immunobiol., vol. 187 (1993) 464–477.

Beeson, Paul B. M.D., "Tolerance to Bacterial Pyrogens", Medical Service, Grady Hospital and the Dept. of Medicine (1947) 39–44.

Bennett–Guerrero, Elliott et al., "Relationship of Preoperative Antiendotoxin Core Antibodies and Adverse Outcomes Following Cardiac Surgery", JAMA, vol. 277, No. 8 (1997) 646–650.

Bhattacharjee, Apurba K. et al., "Affinity–Purified *Escherichia coli* J5 Lipopolysaccharide–Specific IgG Protects Neutropenic Rats Against Gram–Negative Bacterial Sepsis", Journal of Infectious Diseases (1994) 170:622–629.

Bhattacharjee et al., A Noncovalent Complex Vaccine Prepared with Detoxified *Escherichia coli* J5 (Re Chemotype) Lipopolysaccharides and *Neiseria meningitides* Group B Outer Membrane Protein Produces Protective Antibodies Against Gram–Negative Bacteremia, Infectious Diseases (1996) 173:1157–1163.

Bion, Julian F. et al., "Selective decontamination of the digestive tract reduces Gram–negative pulmonary colonization but not systemic endotoxemia in patients undergoing elective liver transplantation", Critical Care Medicine, vol. 22, No. 1 (1994) 40–49.

Bone, Roger C. et al., "Definitions for Sepsis and Organ Failure and Guidelines for the Use of Innovative Therapies in Sepsis", ACCP/SCCM Consensus Conference (1992) 1644–1655.

Boom, S.J. et al., "Abolition of the Hyperdynamic Cardiovascular State Induced by Endotoxaemia with a Murine IgG Monoclonal Antibody to Endotoxin", 12 pages.

Boom, S.J. et al., "Comparison of HA–1A and E5 Monoclonal Antibodies to Endotoxin in Rats with Endotoxaemia", Eur J. Surg, 159, (1993) 559–561.

Bosenberg, A.T. et al., "Strenuous exercise causes systemic endotoxemia", Am. Physiological Society (1988) 106–108.

Brandenburg, Klaus et al., "A comment on the preparation of liposomes from and on the $\beta \leftrightarrows \alpha$ acyl chain melting behavior of rough mutant lipopolysaccharide", Biochimica et Biophysica Acta (1991) 1–4.

Braude, Abraham et al., "Passive Immunization Against the Local Shwartzman Reaction", Journal of Immunology, vol. 108, No. 2 (1972) 505–512.

Brock–Utne, J.G. et al., "Endotoxaemia in exhausted runners after a long race", SAMJ, vol. 73, (1988) 533–536.

Bresee, Joseph S. et al., "Hepatitis C Virus Infection Associated with Administration of Intravenous Immune Globulin", JAMA, vol. 276, No. 19 (1996) 1563–1567.

Brown, Anna et al., "The antibody response to salmonellae in mice and humans studied by immunoblots and ELISA", Microbial Pathogenesis (1989) 6:445–454.

Bruderer, Urs et al., "Qualitative analysis of antibody binding", Journal of Immunological Methods, (1990) 133:263–268.

Bruins, Scott C. et al., "Immunization with R Mutants of *Salmonella minnesota*", Infection and Immunity (1977) 16–20.

Bruins, Scott C. et al., Parameters Affecting the Enzyme–Linked Immunosorbent Assay of Immunoglobulin G Antibody to a Rough Mutant *Salmonella minnesota*, Infection and Immunity (1978) 721–728.

Butler, Patrice et al., "M2 mitochondrial antibodies and urinary rough mutant bacteria in patients with primary biliary cirrhosis and in patients with recurrent bacteriuria", Journal of Hepatology (1993) 17:408–414.

Cafiero, Ferdinando et al., "Prophylaxis of infection with intravenous immunoglobulins plus antibiotic for patients at risk for sepsis undergoing surgery for colorectal cancer: Results of a randomized, multicenter clinical trial", Surgery, vol. 112, No. 1 (1991) 24–31.

Carrico, C. James et al., "Multiple–Organ–Failure Syndrome", Arch Surg, vol. 121 (1986) 196–208.

Cho, Norio et al., Delayed Hypersensitivity in Murine Salmonellosis: Specificity of Footpad Reaction in Mice Infected with Rough Mutants of *Salmonella typhimurium*, Microbiol. Immunol., vol. 27 (2) (1983) 167–175.

Christ, William J. et al., "E5531, a Pure Endotoxin Antagonist of High Potency", Science, vol. 268 (1995) 80–83.

Cohen, J. et al., "Antibody Titres to a Rough–Mutant Strain of *Escherichia coli* in Patients Undergoing Allogeneic Bone–Marrow Transplantation", The Lancet (1987) 8–10.

Cometta, Alain et al., "Prophylactic Intravenous Administration of Standard Immune Globulin as Compared with Core–Lipopolysaccharide Immune Globulin in Patients at High Risk of Postsurgical Infection", N.E. Journal of Medicine, vol. 327, No. 4 (1992) 234–240.

Cremer, Natalie et al., "Influence of Stress on Distribution of Endotoxin in RES Determined by Fluorescein Antibody Technic", Stress on Distribution of Endotoxin in RES (1957) 510–513.

Cross, Alan et al., "Safety and Immunogenicity of a Polyvalent *Escherichia coli* Vaccine in Human Volunteers", Journal of Infectious Diseases (1994) 170:834–40.

Cross, Alan et al., "The Human Antibody Response During Natural Bacteremic Infection with Gram–Negative Bacilli against Lipopolysaccharide Core Determinants", Journal of Infectious Diseases, vol. 160, No. 2 (1989) 225–236.

Crowley, James et al., "Opsonization of serum–sensitive and serum–resistant *Escherichia coli* by rough mutant (Re) antisera", J. Lab. Clin. Med., vol. 99, No. 2 (1982) 197–205.

Cryz, S.J. Jr. et al., "Immunization with a *Pseudomonas aeruginosa* Immunotype 5 O Polysaccharide–Toxin A Conjugate Vaccine: Effect of a Booster Dose on Antibody Levels in Humans", Infection and Immunity, vol. 56, No. 7 (1988) 1829–1830.

Cryz, S.J. et al., "Safety and Immunogenicity of *Escherichia coli* O18 O–Specific Polysaccharide (O–PS)–Toxin A and O–PS–Cholera Toxin Conjugate Vaccines in Humans", Journal of Infectious Diseases (1991) 163:1040–1045.

Cullis, Pieter R. et al., "Liposomes as Pharmaceuticals", 39–72.

Daemen, Toos et al., "Differential Effects of Liposome–Incorporation on Liver Macrophage Activating Potencies of Rough Lipopolysaccharide, Lipid A and Muramyl Dipeptide", Journal of Immunology, vol. 142, No. 7 (1989) 2469–2474.

Dale, Peter A. et al., "Human Vaccination with *Escherichia coli* J5 Mutant Induces Cross–Reactive Bactericidal Antibody Against *Neisseria gonorrhoeae* Lipooligosaccharide", Journal of Infectious Diseases (1992) 166:316–325.

Dancey, George F. et al., "Enhancement of Liposomal Model Membrane Immunogenicity by Incorporation of Lipid A1", Journal of Immunology, vol. 119, No. 6 (1977) 1868–1873.

Danner, Robert L. et al., "Endotoxemia in Human Septic Shock", Chest (1991) 169–175.

Deitch, Edwin A. et al., "Endotoxin–induced bacterial translocation and mucosal permeability: Role of xanthine oxidase, complement activation, and macrophage products", Critical Care Medicine, vol. 19, No. 6 (1991) 785–791.

Deitch, Edwin A., The Role of Intestinal Barrier Failure and Bacterial Translocation in the Development of Systemic Infection and Multiple Organ Failure, Arch Surg, vol. 125 (1990) 403–404.

Deitch, Edwin A., "Bacterial Translocation of the Gut Flora", Journal of Trauma, vol. 30, No. 12, (1990) S184–S189.

DeKievit, Teresa R. et al., "Monoclonal Antibodies That Distinguish Inner Core, Outer Core, and Lipid A Regions of *Pseudomonas aeruginosa* Lipopolysaccharide", Journal of Bacteriology, vol. 176, No. 23 (1994) 7129–7139.

Delahooke, D.M. et al., "Tumor Necrosis Factor Induction by an Aqueous Phenol–Extracted Lipopolysaccharide Complex from Bacteroides Species", Infection and Immunity (1995) 840–846.

Desiderio, James V. et al., "Immunization Against Experimental Murine Salmonellosis with Liposome–Associated O–Antigen", Infection and Immunity, vol. 48, No. 3 (1985) 658–663.

Dijkstra, Jan et al., "A procedure for the efficient incorporation of wild–type lipopolysaccharide into liposomes for use in imunological studies", Journal of Immunological Methods, 114 (1988) 197–205.

Dijkstra, Jan et al., "Altered In Vivo Activity of Liposome–Incorporated Lipopolysaccharide and Lipid A", Infection and Immunity (1989) 3357–3363.

Dijkstra, Jan et al., "Modulation of the Biological Activity of Bacterial Endotoxin by Incorporation into Liposomes", Journal of Immunology, vol. 138, No. 8 (1987) 2663–2670.

Din, Zafeer Z et al., "Effect of pH on Solubility and Ionic State of Lipopolysaccharide Obtained from the Deep Rough Mutant of *Escherichia coli*", Biochemistry 32 (1993) 4579–4586.

Ding, H.F. et al., "Protective immunity induced in mice by detoxified salmonella lipopolysaccharide", J. Med. Microbiol., vol. 31 (1990) 95–102.

DiPadova, F.E. et al, "A Broadly Cross–Protective Monoclonal AntibodyBinding to *Escherichia coli* and Salmonella Lipopolysaccharides", Infection and Immunity, vol. 61, No. 9, Sep. (1993) 3863–3872.

DiPadova, Franco E. et al., "Anti–Lipopolysaccharide Core Antibodies", Bacterial Endotoxins: Basic Science (1994) 85–94.

Dominioni, Lorenzo et al., "Effects of High–Dose IgG on Survival of Surgical Patients with Sepsis Scores of 20 or Greater", Arch Surg, vol. 126 (1991) 236–240.

Donnelly, John J. et al., "Immunogenicity of a *Haemophilus influenzae* Polysaccharide–*Neisseria meningitides* Outer Membrane Protein Complex Conjugate Vaccine", Journal of Immunology, vol. 145, No. 9 (1990) 3071–3079.

Dunn, David L. et al., "Immunotherapy of gram–negative bacterial sepsis: Enhanced survival in a guinea pig model by use of rabbit antiserum to *Escherichia coli* J5", Surgery (1980) 212–219.

Elkins, Karen L. et al., "Specific Immunological Unresponsiveness to Bacterial Lipopolysaccharides Develops in a Cyclic Manner", Infection and Immunity, vol. 57, No. 7 (1989) 2253–2255.

Evans, Martin E. et al., "Lipopolysaccharide Heterogeneity in *Escherichia coli* J5 Variants: Analysis by Flow Cytometry", Journal of Infectious Disease (1992) 803–811.

Evans, Martin E. eta l., "Fluorescence–Activated Cell Sorter Analysis of Binding by Lipopolysaccharide–Specific Monoclonal Antibodies to Gram–Negative Bacteria", Journal of Infectious Diseases (1990) 148–155.

Field, Sue et al., "Development of an anti–idiotype monoclonal antibody mimicking the structure of lipopolysaccharide (LPS) inner–core determinants", Microbial Pathogenesis (1993) 15: 103–120.

Field, Susan et al., "An Anti–Idiotype Antibody Which Mimics the Inner–Core Region of Lipopolysaccharide Protects Mice against a Lethal Challenge with Endotoxin", Infection and Immunity, vol. 62 (1994) 3994–3999.

Fink, Mitchell P. et al., "Increased Intestinal Permeability in Endotoxic Pigs", Arch Surg, vol. 126 (1991) 211–218.

Fink, Mitchell P., Effect of Critical Illness on Microbial Translocation and Gastrointestinal Mucosa Permeability, Seminars in Respiratory Infections, vol. 9, No. 4 (1994) 256–260.

Fisher, C.J. Jr. et al., "Immunotherapy of Sepsis Syndrome: A Comparison of the Available Treatments", Klin Wochenschr (1991) 162–167.

Fisher, Charles J. Jr. et al., "Treatment of Septic Shock with the Tumor Necrosis Factor Receptor:Fc Fusion Protein", N.E. Journal of Medicine, vol. 334, No. 26 (1996) 1697–1702.

Fong, Yuman et al., "Endotoxemia Elicits Increased Circulating $\beta x$–IFN/IL–6 in Man", Journal of Immunology, vol. 142, No. 7 (1989) 2321–2324.

Ford, Edward G. et al., "Sepsis After Coronary Bypass Grafting: Evidence for Loss of the Gut Mucosal Barrier", Ann Thorac Surg (1991) 514–517.

Freed, Gary L. et al., "Safety of Vaccinations, Miss America, the Media and Public Health", JAMA, vol. 276, No. 23 (1996) 1869–1872.

Freeman, R. et al., "Prevention of fever and Gram negative infection after open heart surgery by antiendotoxin", Thorax (1985) 40: 846–848.

Freudenberg, M.A. et al., "Analysis of LPS released from *Salmonella abortus equi* in human serum", Microbial Pathogenesis (1991) 10: 93–104.

Fries, Louis F. et al., "Liposomal malaria vaccine in humans: A safe and potent adjuvant strategy", Proc. Natl. Acad. Sci. USA, vol. 89 (1992) 358–362.

Gaffin, S.L. et al., "Hypoxia–Induced Endotoxemia in Primates: Role of Reticuloendothelial System Function and Anti–Lipopolysaccharide Plasma", Aviation, Space and Environmental Medicine (1986) 1044–1049.

Gaffin, S.L. et al., "The use of antilipopolysaccharide (anti–LPS) antibodies in the management of septic shock", SA Mediese Tydskrif Deel 65 (1984) 158–161.

Gaffin, Stephen L. et al., "An ELISA procedure for detecting human anti–endotoxin antibodies in serum", Ann Clin Biochem (1983) 19: 191–194.

Gaffin, Stephen L., "Large–Scale Production of Anti–Gram Negative Bacterial Antibodies", The Lancet (1983) 1420–1421.

Gaffin, Stephen L., "Anti–lipopolysaccharide toxin therapy for whole body X–irradiation overdoes", The British Journal of Radiology (1985) 58: 881–884.

Gaffin, S.L. et al., "A morphological study of the action of equine anti–lipopolysaccharide plasma on gram–negative bacteria", J. Med. Microbiol., vol. 24 (1987) 165–168.

Gaffin, Stephen L. et al., "Effect of corticosteroid prophylaxis on lipopolysaccharide levels associated with intestinal ischemia in cats", Critical Care Medicine, vol. 14, No. 10 (1986) 889–891.

Gaffin, Stephen L. et al., "Properties of Human Anti–Lipopolysaccharide Gamma Globulin: Specificity and Protective Effects", Vox Sang (1985) 48: 276–283.

Galanos, Chris et al., "Mechanisms of Endotoxin Shock and Endotoxin Hypersensitivity", Immunobiol., vol. 187 (1993) 346–356.

Gathiram, P. et al., "Time Course of Endotoxemia and Cardiovascular Changes in Heat–Stressed Primates", Aviation, Space and Environmental Medicine (1987) 1071–1074.

Gathiram, P. et al., Superior Mesenteric Artery Occlusion Shock in Cats: Modification of the Endotoxemia by Antilipopolysaccharide Antibodies (Anti–LPS), Circulatory Shock (1986) 19: 231–237.

Gathiram, P. et al., "Antilipopolysaccharide Improves Survival in Primates Subjected to Heat Stroke", Circulatory Shock (1987) 23: 157–164.

Gazzano–Santoro, Helene, "Competition between $rBPI_{23}$, a Recombinant Fragment of Bactericidal/Permeability–Increasing Protein, and Lipopolysaccharide (LPS)–Binding Protein for Binding to LPS and Gram–Negative Bacteria", Infection and Immunity (1994) 1185–1191.

Gigliotti, Francis et al., "Failure of Monoclonal Antibodies to Core Glycolipid to Bind Intact Smooth Strains of *Escherichia coli*", The Journal of Infectious Diseases, vol. 151, No. 6 (1985) 1005–1011.

Gmeiner, Jobst et al., "Molecular Composition of the Outer Membrane of *Escherichia coli* and the Importance of Protein–Lipopolysaccharide Interactions", Arch Microgiol., vol. 127 (1980) 81–86.

Goldie, Anne S. et al., "Natural Cytokine Antagonists and Endogeneous Antiendotoxin Core Antibodies in Sepsis Syndrome", JAMA, vol. 274, No. 3 (1995) 172–177.

Goto, Masakatsu et al., "Early Endotoxin Tolerance in Suckling Rats", Research in Communications and Chemical Pathology and Pharmacology, vol. 76, No. 2 (1992) 249–252.

Goris, Jan A. et al., "Multiple–Organ Failure", Arch Surg, vol. 120 (1985) 1109–1115.

Gould, F.K. et al., "Antibody to endotoxin is associated with decreased frequency of postoperative infection", Am J Obstet Gynecol (1988) 317–319.

Gregoriadis, Gregory, "Immunological adjuvants: a role for liposomes", Immunology Today, vol. 11, No. 3 (1990) 89–97.

Green, S. et al., "Liposomal Vaccines. Advances in Experimental Medicine and Biology" vol. 383, (1995) 83–92.

Greenman, Richard L. et al., "A Controlled Clinical Trial of E5 Murine Monoclonal IgM Antibody to Endotoxin in the Treatment of Gram–Negative Sepsis", JAMA, vol. 266, No. 8 (1991) 1097–1102.

Greisman, Sheldon E. M.D. et al., "Mechanisms of Endotoxin Tolerance, II. Relationship Between Endotoxin Tolerance and Reticuloendothelial System Phagocytic Activity in Man", Journal of Experimental Medicine, vol. 119 (1963) 241–264.

Greisman, Sheldon E. et al., "Comparative Pyrogenic Reactivity of Rabbit and Man to Bacterial Endotoxin", PSEBM, vol. 131 (1969) 1154–1158.

Greisman, Sheldon E. et al., "Mechanisms of Endotoxin Tolerance, I. Relationship Between Tolerance and Reticuloendothelial System Phagocytic Activity in the Rabbit", Journal of Experimental Medicine, (1962) 663–674.

Greisman, Sheldon E. et al., "Mechanisms of Endotoxin Tolerance with Special Reference to Man", Journal of Infectious Diseases, vol. 128 (1973) S265–S276.

Greisman, Sheldon E. et al., "Mechanisms of Endotoxin Tolerance, V. Specificity of the Early and Late Phases of Pyrogenic Tolerance", The Journal of Immunology, vol. 103, No. 6 (1969) 1223–1236.

Greisman, Sheldon E., "Induction of Endotoxin Tolerance", Beneficial Effects of Endotoxins (1983) 149–178.

Greisman, Sheldon E. et al., "Experimental Gram–Negative Bacterial Sepsis: Prevention of Mortality Not Preventable by Antibiotics Alone", Infection and Immunity, vol. 25 (1979) 538–557.

Gruner, Sol. M. et al., "Materials Properties of Liposomal Bilayers" 1–38.

Haishima, Yuji et al., "Structural investigation on the lipopolysaccharide of *Escherichia coli* rough mutant F653 representing the R3 core type", Eur. J. Biochem., vol. 203 (1992) 127–134.

Hancock et al., "E. Preparation of Lipopolysacharide and Enterobacterial Common Antigen", Bacterial Cell Surface Techniques 91–97.

Hansorough, John M.D. et al., "Effects of Recombinant Bactericidal/Permeability–Increasing Protein ($rBPI_{23}$) on Neutrophil Activity in Burned Rats", Journal of Trauma: Injury, Infection, and Critical Care, vol. 40, No. 6 (1996) 886–893.

Hodgson, Christopher J. et al., "Prophylactic use of human endotoxin–core hyperimmune gammaglobulin to prevent endotoxaemia in colostrums–deprived gnotobiotic lambs challenged orally with *Escherichia coli*", FEMS Immunology and Medical Microbiology vol. 11 No. 3 (1995) 83–92.

Hodgson, Christopher J. et al., "Prophylactic use of human endotoxin–core hyperimmune gammaglobulin to prevent endotoxaemia in colostrums–deprived gnotobiotic lambs challenged orally with *Escherichia coli*", FEMS Immunology and Medical Microbiology vol. 11 (1995) 171–180.

Hoffman, William D. et al., "Endotoxin in Septic Shock", Anesth. Analg. (1993) 77: 613–624.

Inzana, Thomas J. Ph.D. et al., "Immune response to cattle to *Haemophilus somnus* lipid A–protein conjugate vaccine and efficacy in a mouse abortion model", Am J Vet Res, vol. 53, No. 2 (1992) 175–179.

Jackson et al., "Lactam Antibiotic–Induced Release of Free Endotoxin: In Vitro Comparison of Penicillin–Binding Protein (PBP) 2–Specific Imipenem and PBP 3–Specific . . . ", Merck Institute for Therapeutic Research (1992) 1033–1041.

Jarvis et al., "Infection with hepatitis G virus among recipients of plasma products", The Lancet (1996) 348: 1352–1355.

Jones et al., "Controlled Trial of Pseudomonas Immunoglobulin and Vaccine in Burn Patients", The Lancet (1980) 1263–1265.

Jones et al., "Controlled Trials of Polyvalent Pseudomonas Vaccine in Burns", The Lancet (1979) 977–983.

Jones, R.J., "Early Protection by Vaccines in Burns", Br. J. exp. Path. (1971) 52: 100–109.

Jones, R.J., "Specificity of early protective responses induced by pseudomonas vaccines", J. Hyg. Camb. (1972) 70: 343–351.

Kreger, Bernard A. et al., "Gram–Negative Bacteremia, III. Reassessment of Etiology, Epidemiology and Ecology in 612 Patients", Am. Journal of Medicine, vol. 68 (1980) 332–343.

Konstantinov, G. et al., "Passive Protection Against Heterologous Gram–Negative Bacteria Mediated by Antiserum to Epimeraseless Re Mutant of *Salmonella minnesota*", Ann. Immunol. (Inst. Pasteur) (1982) 133: 71–76.

Kress, H.G. et al., "Prediction and Prevention, by Immunological Means, of Septic Complications After Elective Cardiac Surgery", Second Vienna Shock Forum (1989) 1031–1035.

Kuppermann, Nathan et al., "Comparison of a Recombinant Endotoxin–Neutralizing Protein with a Human Monoclonal Antibody to Endotoxin for the Treatment of *Escherichia coli* Sepsis in Rats", The Journal of Infectious Disease (1994) 170: 630–635.

Lachman, Eylon et al., "Anti–Lipopolysaccharide Immunotherapy in Management of Septic Shock of Obstetric and Gynaecological Origin", The Lancet (1984) 981–983.

Girardin, Eric et al., "Treatment of Severe Infectious Purpura in Children with Human Plasma from Donors Immunized with *Escherichia coli* J5: A Prospective Double–Blind Study", The Journal of Infectious Diseases (1992) 165: 695–701.

Luderitz, O. et al., "Immunochemistry of O and R Antigens of Salmonella and Related Enterobacteriaceae", Bacteriological Reviews, vol. 30, No. 1 (1966) 192–255.

Manning et al., "Molecular Cloning and Expression in *Escherichia col* K–12 of the O Antigens of the INaba and Ogawa Serotypes of the *Vibrio cholerae* O1 Lippopolysaccharides and Their Potention for Vaccicen Development", Infection and Immunity (1986) 53:272–277.

Marks, Melvin et al., "Induction of Immunity against Lethal *Haemophilus influenzae* by *Escherichia coli* Core Lipopolysaccharide", J. Clin. Invest., vol. 69 (1982) 742–749.

Martich, G. Daniel et al., "Response of Man to Endotoxin", Critical Care Medicine Department, 8 pp.

Mattsby–Baltzer, Inger et al., "Antibodies to Lipid A: Occurrence in Humans", Reviews of Infectious Diseases, vol. 6, No. 4 (1984) 553–557.

Mattsby–Baltzer, I. Et al., "Susceptibility of Lipopolysaccharide–Responsive and –Hyporesponsive $Ity^s$ Mice to Infection with Rough Mutants of *Salmonella typhimurium*", Infection and Immunity, vol. 64, No. 4 (1996) 1321–1327.

McCabe, William R. et al., "Type–Specific and Cross–Reactive Antibodies in Gram–Negative Bacteremia", The N.E. Journal of Medicine, vol. 287, No. 6 (1972) 261–267.

McCabe, William R. et al., "Immunization With R Mutants of S. Minnesota, I. Protection against CHallenge with Heterologous Gram–Negative Bacilli", The Journal of Immunology, vol. 108, No. 3 (1972) 601–610.

McCallus, Daniel et al,. "Antibody Specific for *Escherichia coli* J5 Cross–Reacts to Various Degrees with an *Escherichia coli* Clinical Isolate Grown for Different Lengths of Time", Infection and Immunity, vol. 55, No. 5 (1987) 1042–1046.

Mehta, N.D. et al., "Comparison of the opsonic activity of polyclonal and monoclonal antibodies raised against *Salmonella minnesota* strain R595", J. Med. Microbiol., vol. 25 (1988) 85–93.

Mehta, N.E. et al., A comparison of specificity and biological activity of polyclonal and monoclonal antibodies raised against *Salmonella minnesota* R595 lipopolysaccharide, J. Med Micriobiol., vol. 31 (1990) 85–93.

Michael, J. Gabriel et al., "Immune Response to Parental and Rough Mutant Strains of *Salmonella minnesota*", Infection and Immunity, vol. 33, No. 3 (1981) 784–787.

Michie, Hamish R. et al., "Detection of Circulating Tumor Necrosis Factor After Endotoxin Administration", N.E. Journal of Medicine (1988) 318: 1481–1486.

Miyata, Tadanori, "Endotoxaemia Pulmonary Complications, and Thrombocytopenia in Liver Transplantation", The Lancet (1989) 189–191.

Moore, Frederick et al., "Gut Bacterial Translocation via the Portal Vein: A Clinical Perspective with Major Torso Trauma", Journal of Trauma, vol. 31, No. 5 (1991) 629–638.

Morris, Debra et al., "Endotoxemia in neonatal calves given antiserum to a mutant *Escherichia coli* (J5)", Am J Vet Res, vol. 47, No. 12 (1986) 2554–2565.

Morris, Debra et al., "Evaluation of the opsonic capacity of core lipopolysaccharide antiserum of equine origin against smooth *Escherichia coli* 0111:B4, using macrophage chemiluminescence", Am J Vet Res, vol. 50, No. 8 (1989) 1272–1278.

Mulholland, John J. et al,. "Quantitative Studies of Febrile Tolerance and Levels of Specific Antibody Evoked by Bacterial Endotoxin", Journal of Clinical Investigation, vol. 44, No. 6 (1965) 920–928.

Mutharia, Lucy M. et al., "Monoclonal Antibodies Specific for *Escherichia coli* J5 Lipopolysaccharide: Cross–Reaction with Other Gram–Negative Bacterial Species", Infection and Immunity, vol. 45, No. 3 (1984) 631–636.

Munster, Andrew M. et al., "Translocation: Incidental Phenomenon or True Pathology?", Annals of Surgery, vol. 218, No. 3 (1993) 321–327.

Nelson, D. et al., "Influence of subinhibitory levels of antibiotics on expression of *Escherichia coli* lipopolysaccharide and binding of anti–lipopolysaccharide monoclonal antibodies", J. Med Microbiol., vol. 39 (1993) 100–106.

Nelson, J.W. et al., "Production and characterization of mouse monoclonal antibodies reactive with the lipopolysaccharide core of *Pseudomonas aeruginosa*", J. Med. Microbiol., vol. 36 (1992) 358–365.

Nelson, Douglas et al., "Recombinant endotoxin neutralizing protein improves survival from *Escherichia coli* sepsis in rats", Critical Care Medicine, vol. 23, No. 1 (1995) 92–98.

Nevola, Joseph J. et a., "Colonization of the Mouse Intestine by an Avirulent *Salmonella typhimurium* Strain and Its Lipopolysaccharide–Defective Mutants", Infection and Immunity, vol. 50, No. (1985) 152–159.

Ng, Ah–Kau et al., "Relationship of Structure to Function in Bacterial Endotoxins: Serologically Cross-reactive Components and their Effect on Protection of Mice Against Some Gran–negative Infections", J. Gen. Microbiol. (1976) 94: 107–116.

Nikaido, Hiroshi et al., "Outer Membrane of *Salmonella typhimurium*: Electron Spin Resonance Studies", Biochimica et Biophysica Acta (1977) 465: 152–164.

Nys, Monique et al., "Protective Effects of Polyclonal Sera and Monoclonal Antibodies Active to *Salmonella minnesota* Re595 Lipopolysaccharide during Experimental Endotoxemia", Journal of Infectious Diseases (1990) 162: 1087–1095.

Ohshio, Gakuji et al., "The Effect of Splenectomy on Antibody Response to Lipopolysaccharide (*E. coli*) Immunization", Journal of Trauma, vol. 28, No. 3 (1988) 379–382.

Overbeek, Berry P. et al., "Carumonam Enhances Reactivity of *Escherichia coli* with Mono– and Polyclonal Antisera to Rough Mutant *Escherichia coli* J5", Journal of Clinical Microbiology, vol. 25, No. 6 (1987) 1009–1013.

Papa, M. et al., "The Effect of Ischemia of the Dog's Colon on Transmural Migration of Bacteria and Endotoxin", Journal of Surgical Research (1983) 35: 264–269.

Parent, James B. et al., "Reactivity of Monoclonal Antibody E5® With Endotoxin. II Binding to Short– and Long–Chain Smooth Lipopolysaccharides", Circulatory Shock (1992) 38: 63–73.

Peter, G. et al., "Limited Protective Effect of Rough Mutant Antisera in Murine *Escherichia coli* Bacteremia", Infection 10 (1982) 228–232.

Petrov, Alexander B. et al., "Non–specific modulation of the immune response with liposomal meningococcal lipopolysaccharide: role of different cells and cytokines", 7 pp.

Pilz, Gunter et al., "Early Sepsis Treatment with Immunoglobulins After Cardiac Surgery in Score–identified High–risk Patients", Chest (1994) 76–82.

Pollack, Matthew et al., "Enhanced Survival in *Pseudomonas aeruginosa* Septicemia Associated with High Levels of Circulating Antibody to *Escherichia–coli* Endotoxin Core", The Journal of Investigation, vol. 72 (1983) 1874–1881.

Pollack, Matthew et al., "Specificity and Cross–Reactivity of Monoclonal Antibodies Reactive with the Core and Lipid A Regions of Bacterial Lipopolysaccharide", The Journal of Infectious Diseases, vol. 159, No. 2 (1989) 168–188.

Poxton, Ian R. et al., "Biological Activity of Bacteriodes Lipopolysaccharide–Reappraisal", Clinical Infectious Diseases (1995) 20: S149–S153.

Poxton, I.R., "Antibodies to lipopolysaccharide", Journal of Immunological Methods, 1995.

Quezado, Zenaide M.N. et al., "A Controlled Trial of HA–1A in a Canine Model of Gram–negative Septic Shock", JAMA, vol. 269, No. 17 (1993) 2221–2227.

Raetz, Christian R. H., "Bacterial Lipopolysaccharides: a Remarkable Family of Bioactive Macroamphilpiles", Chapter 69, (1995) 1–69.

Sakulramrung, Reutai et al., Cross–Reactive Immunoprotective Antibodies to *Escherichia coli* 0111 Rough Mutant J5, The Journal of Infectious Diseases, vol. 151, No. 6 (1985) 995–1003.

Sakulramrung, R. et al., "Antigenic and Immunogenic Characteristics of Subcellular Fractions and Whole Cells of a Rough *E. coli* 0111 (J5) Mutant", Immunobiol. vol. 169 (1985) 372–388.

Saladino, Richard et al., "Efficacy of a Recombinant Endotoxin Neutralizing Protein in Rabbits with *Escherichia coli* Sepsis", Circulatory Shock (1994) 42: 104–110.

Schlecht, S. et al., "Nachweis von Antikorpern gegen Salmonella–R–Antigene in Salmonella–O–Antiseren", Zbl. Bakt. I. Abt. Orig. (1971) A 216: 472–482. English Abstract Only, reference does not include all pages cited.

Schlecht et al., "Protective Role of Salmonella R Mutants in Salmonella Infection in Mice", Zbl. Bakt. Hug. I. Abt. Orig. (1979) A 245:71–88. English Abstract Only, reference does not include all pages cited.

Schlecht, "Active Immunication to Experimental Salmonellosis in Mice Protective Properties of Salmonella R Mutants Against Infection with Different Pathogenic Salmonella Infection in Mice,", Zbl, Bakt., Hug. I. Abt. Orig. A (1981) 249:362–372. English Abstract Only, reference does not include all pages cited.

Schulkind, M.L. et al., "The Specific Secondary Biological Activities of Rabbit IgM and IgG Anti–*Salmonella typhimurium* 'O' Antibodies Isolated During the Development of the Immune Response", Immunology (1972) 23: 159–170.

Schwartzer, T.A. et al., "Immunochemical Specificity of Human Antibodies to Lipopolysaccharide from the J5 Rough Mutant of *Escherichia coli* )111:B4", The Journal of Infectious Disease, vol. 159, No. 1 (1989) 35–42.

Senior, Judith et al., "Dehydration–rehydration vesicle methodology facilitates a novel approach to antibody binding to liposomes", Biochimica et Biophysica Acta (1989) 1003: 58–62.

Shenep, Jerry L. et al., "Role of Antibiotic Class in the Rate of Liberation of Endotoxin During Therapy for Experimental Gran–Negative Bacterial Sepsis", The Journal of Infectious Diseases, vol. 151, No. 6 (1985) 1012–1018.

Somerville, John E. et al., "A Novel *Escherichia coli* Lipid A Mutant that Produces an Anti–inflammatory Lipopolysaccharide", J. Clin. Invest., vol. 97, No. 2 (1996) 359–365.

Stack, Anne E. et al., "Failure of prophylactic and therapeutic use of a murine anti–tumor necrosis factor monoclonal antibody in *Escherichia coli* sepsis in the rabbit", Critical Care Medicine, vol. 23, No. 9 (1995) 1512–1518.

Su, Shidong et al,. "Analysis of the Immune Response to Lipopolysaccharide", The Journal of Immunology, vol. 145, No. 9 (1990) 2994–3001.

Suffredini, Anthony F. et al., "The Cardiovascular Response of Normal Humans to the Administration of Endotoxin", N.E. Journal of Medicine (1989) 280–287.

Tamauchi et al., "Enhancement of immunogenicity by incorporation of lipid A into liposomal model membranes and its application to membrane–associated antigens" (1983) 50: 605–612.

Tonoli, M. et al., The anti–lipid A antibody HA–1A binds to rough Gram–negative bacteria fixes complement and facilitates binding to erythrocyte CRI (CD35), Clin. Exp. Immunol. (1993) 92: 232–238.

Trautmann, M. et al., "Antiserum Against *Escherichia coli* J5: A Re–evaluation of its In vitro and In vivo Activity Against Heterologous Gram–negative Bacteria", Infectious 13 (1985) 140–145.

Tsal, Chao–Ming et al., "Heterogeneity and Variation Among *Neisseria meningitides* Lipopolysaccharides", Journal of Bacteriology, vol. 155, No. 2 (1983) 498–504.

United States Pharmacopeia, "Pyrogen Test", The National Formulary, USP 23, NF 18, (1995) 151.

Van Deventer, Sander et al., "Endotoxaemia: An Early Predictor of Septicaemia in Febrile Patients", The Lancet (1988) 605–608.

Van Rooijen et al., "Endotoxin Enhanced Adjuvant Effect of Liposomes, Particularly When Antigen and Endotoxin are Incorporated within the Same Liposome", Immunological Communications (1980) 747–757.

Warren, H. Shaw et al., "Sounding Board—Anti–Endotoxin Monoclonal Antibodies", vol. 326, No. 17 (1992) 1153–1157.

Warren, H. Shaw et al., "Assessment of Ability of Murine and Human Anti–lipid A Monoclonal Antibodies to Bind and Neutralize Lipopolysaccharide", J. Exp. Med., vol. 177 (1993) 89–97.

Warren, H.S. et al., "Endotoxin Neutralization with Rabbit Antisera to *Escherichia coli* J5 and Other Gram–Negative Bacteria", Infection and Immunity, vol. 55 (1987) 1668–1673.

Wassef, Nabila M. et al., "Liposomes as Carriers for Vaccines", Immunomethods (1994) 4: 217–222.

Weintraub, Andrej et al., "Chemical and Immunochemical Analyses of *Bacteroides fragilis* Lipoplysaccharides", Infection and Immunity (1995) 197–201.

Wells et al., "Anti–pseudomonas activity of anti–lipopolysaccharide hyperimmune equine plasma", Clin. Exp. Immunol. (1987) 68: 86–92.

Wells et al., "Radiaton Induced Gram Negative Bacteremia and Endotoxemia in Rabbits: Modification by Anti–Lipopolysacharide Hyperimmune Equine Plasma", Life Sciences, vol. 40 (1987) 2543–2550.

Wells et al., "Anti–LPS Antibodies Reduce Endotoxemia in Whole Body $^{60}$Co Irradiated Primates: A Preliminary Report", Aviation, Space and Environmental Medicine (1990) 802–806.

Wells et al., "Properties of equine anti–lipopolysaccharide hyperimmune plasma: binding to lipopolysaccharide and bactericidal activity against gram–negative bacteria", J. Med M.icrobiol., vol. 24 (1987) 187–196.

Wolff, Sheldon et al., "Quantitative aspects of the pyrogenic response of rabbits to endotoxin", Lab. Clin. Investigations (1965) 268–276.

Wong et al., "Liposome potentiation of humoral immune response to lipopolysaccharide and O–polysaccharide antigens of *Brucella abortus*,", Immunology (1992) 77: 123–128.

Wood, David et al., "Reactivity of Monoclonal Antibody E5® with Endotoxin", Circulatory Shock (1992) 38: 55–62.

Zellner, P.R. et al., "Active Immunization against *Pseudomonas aeruginosa* in Burns", 499–508.

Alving et al., Liposomes as Carriers of Peptide Antigens: Induction of Antibodies and Cytotoxic T Lymphocytes to Conjugated and Unconjugated Peptides, Immunological Reviews, No. 145 pp. 5–31 (1995).

Antonov et al., Synthesis and Serological Characterization of L–glycero–ά–D–manno–hepotopyranose–containing di– and tri–saccharides of the non–reducing terminus of the *Escherichia coli* K–12 LPS core Oligosaccharide, Carbohydrate Research 314:85–93 (1998).

Appelmelk et al., Production and Characterization of Mouse Monoclonal Antibodies Reacting with the lipopolysaccharide Core Region of Gram–Negative Bacilli, J. Med. Microbiol. 26:107–114 (1988).

Aydintug et al., Cross–Reactivity of Monoclonal Antibodies to *Escherichia coli* J5 with Heterologous Gram–Negative Bacteria and Extracted Lipopolysaccharides, J. Infectious Diseases 160:846–857 (1989).

Bakouche et al., Enhancement of Immunogenicity of Tumour Virus Antigen by Liposomes: The Effect of Lipid Composition, Immunology 58:507–513 (1986).

Bakouche et al., Impairment of Immunogenicity by Antigen Presentation in Liposomes Made from Dimyristoylphosphatidyl–Ethanolamine Linked to the Secretion of Prostaglandins by Macrophages, Eur. J. Immunol. 17:1839–1842 (1987).

Banerji et al., Membrane Lipid Composition Modulates the Binding Specificity of a Monoclonal Antibody Against Liposomes, Biochimica et Biopysica Acta 689:319–326 (1982).

Barclay, Endogenous Endotoxin–Core Antibody (Endo-CAb) as a Marker of Endotoxin Exposure and a Prognostic Indicator: A Review, Bacterial Endotoxins: Lipopolysaccharides From Genes to Therapy, pp. 263–272, 1995 Wiley–Liss, Inc.

Baumgartner et al., Antibodies to Lipopolysaccharides after Immunication of Humans with the Rough Mutant *Escherichia coli* J5, J. Infectious Diseases 163:769–772 (1991).

Bjornson et al., Specificity of Immunoglobulin M Antibodies in Normal Human Serum That Participate in Opsonophagocytosis and Intracellular Killing of *Bacteroides fragilis* and *Bacteroides thetaiotaomicron* by Human Polymorphonuclear Leukocytes, Infection and Immunity 30:263–271 (1980).

Brade et al., The Immunogenicity and Antigenicity of Lipid A Are Influenced by its Physicochemical State and Environment, Infection and Immunity 55:2636–2644 (1987).

Campbell et al., Immunogenicity of 24–Valent Klebsiella Capsular Polysaccharide Vaccine and an Eight–Valent Pseudomonas O–Polysaccharide Conjugate Vaccine Administered to Victims of Acute Trauma, Clinical Infectious Disease 23:179–181 (1996).

Chanderbhan et al., Sterol Carrier Protein$_2$: Further Evidence for its Role in Adrenal Steroidogenesis, Endocrine Research 12:351–370 (1986).

Chedid et al., A Proposed Mechanism for Natural Immunity to Enterobacterial Pathogens, J. Immunology 100:292–301 (1968).

Cohen et al., Double–blind Vaccine–Controlled Randomised Efficacy Trial of an Investigational *Shigella sonnei* Conjugate Vaccine in Young Adults, The Lancet 349:155–159 (1997).

Cryz, Jr. et al., Effects of Chemical and Heat Inactivation on the Antigenicity and Immunogenicity of *Vibrio cholerae*, Infection and Immunity 38:21–26 (1982).

Cryz Jr. et al., Safety and Immunogenicity of a *Pseudomonas aeruginosa* O–Polysaccharide Toxin A Conjugate Vaccine in Humans, J. Clin. Invest. 80:51–56 (1987).

DeMaria et al., Immunization with Rough Mutants of *Salmonella minnesota*: Initial Studies in Human Subjects, J. Infectious Diseases 158:301–311 (1988).

De Padova et al., A Broadly Cross–Protective Monoclonal Antibody Binding to *Escherichia coli* and *Salmonella lipopolysaccharides*, Infection and Immunity 61:3863–3872 (1993).

Dlabac et al., Pathogenicity and Protective Effect of Rough Mutants of Salmonella Species in Germ–Free Piglets, Infection and Immunity 65:5238–5243 (1997).

Fagelman et al., Simulated Surgical Wound Infection in Mice, Arch. Surg. 116:761–764 (1981).

Fricks and Hogle, Cell–Induced Conformational Change in Poliovirus: Externalization of the Amino Terminus of VP1 is Responsible for Liposome Binding, J. Virology 64:1934–1945 (1990).

Galanos et al., Immunogenic Properties of Lipid A, Review of Infectious Diseases 6:546–556 (1984).

Galanos et al., Lipopolysaccharide: Properties of an Amphipathic Molecule, Handbook of Endotoxin vol. 1: Chemistry of Endotoxin, pp. 46–58 (1984).

Gerlier et al., Liposomes as a Tool to Study the Role of Membrane Presentation in the Immunogenicity of a MuL-V–Related Tumor Antigen, J. Immunology 131:485–490 (1983).

Giardino et al., Characteristics of Systemic Antbody Responses of Nonhuman Primates Following Active Immunization with *Porphyromonas gingivalis*, *Prevotella intermedia* and Bacteroides Fragilis, Oral Microbiol Immunol 11:79–87 (1996).

Garnier et al., Enhancement of In Vivo and In Vitro T Cell Response Against Measles Virus Haemagglutinin After its Incorporation into Liposomes: Effect of the Phospholipid Composition, Vaccine 9:340–345 (1991).

Gerlier et al., Efficient Major Histocompatibility Complex Class II–restricted Presentation of Measles Virus Relies on Hemagglutinin–mediated Targeting to its Cellular Receptor Human CD46 Expressed by Murine B Cells, J. Exp. Med. 179:353–358 (1994).

Gerlier et al., Induction of Antibody Response to Liposome–Associated Gross–Virus Cell–Surface Antigen (GCSAa) Br. J. Cancer 41:236–242 (1980).

Dijkstra, Chapter 5: A Comparison of Methods for the Preparation of Lipopolysaccharide–Containing Liposomes, Liposome Technology $2^{nd}$ Edition, vol. II Entrapment of Drugs and Other Materials, edited by Gregoriadis, CRC Press, London (1993).

Greisman et al., Experiment Gram–Negative Bacterial Sepsis: Reevaluation of the Ability of Rough Mutant Antisera to Protect Mice (40231), Proceedings of the Society for Experimental Biology and Medicine 158:482–490 (1978).

Gupta et al., Comparative Immunogenicity of Conjugates Composed of *Escherichia coli* O111 O–Specific Polysaccharide, Prepared by Treatment with Acetic Acid or Hydrazine, Bound to Tetanus Toxoid by Two Synthetic Schemes, Infection and Immunity 63:2805–2810 (1995).

Hamilton–Davies et al., Endotoxin Immune Status and Protection Against Multiple Organ Dysfunction Syndrome in the Surgical Patient, pp. 24–38.

Hodgin et al,. Effect of Active and Passive Immunizations with Lipid A and *Salmonella minnesota* Re 595 on Gram–Negative Infections in Mice, Infection 4:5–10 (1976).

Ivanoff et al., Secondary Immune Response to Oral and Nasal Rough Mutant Strains of *Salmonella typhimurium*, Ann. Immunol. (Inst. Pasteur) 133:61–70 (1982).

Jansson et al., Structural Studies on the Hexose Region of the Core in Lipopolysaccharides from Enterobacteriaceae, Eur. J. Biochem. 115:571–577 (1981).

Johns et al., Immunization with R Mutants of *Salmonella minnesota* II. Serological Response to Lipid A and the Lipopolysaccharide of Re Mutants, Infection and Immunity 17:9–15 (1977).

De Jongh–Leuvenink et al., Detection of Antibodies Against Lipopolysaccharides of *Escherichia coli* and Salmonella R and S Strains by Immunoblotting, Infection and Immunity 50:716–720 (1985).

Kasper et al., Quantitative Determination of the Antibody Response and the Capsular Polysaccharide of *Bacteroides fragilis* in an Animal Model of Intraabdominal Abscess Formation, J. Infectious Diseases 156:789–795 (1977).

Kenney et al., Antibody Responses in Rabbits to *Salmonella minnesota* R–Mutants, Zbl. Bakt. Hyg. I. Abt. Orig. A 217:183–197 (1971).

Levi et al., Development of Multivalent Live Vaccine Active Against a Wide Range of Enterobacteriaceae, New Developments with Human and Veterinary Vaccines, pp. 119–123, Alan R. Liss, Inc. New York (1980).

Lugowski et al., Characterization and Diagnostic Application of a Lipopolysaccharide Core Oligosaccharide–Protein Conjugate, J. Immunological Methods 95:187–194 (1986).

Lugowski et al., Immunochemical Characterization of Citrobacter Strain PCM 1487 O–specific Polysaccharide– and Core Oligosaccharide–Protein Conjugates, FEMS Microbiology Immunology 89:201–208 (1992).

Lugowski et al., Serological Characterization of Anti–Endotoxin Sera Directed Against the Conjugates of Oligosaccharide Core of *Escherichia coli* type R1, R2, R3, J5 and Salmonella Ra with Tetanus Toxoid, FEMS Immunology and Medical Microbiology 16:21–30 (1996).

Lugowski et al., Anti–endotoxin Antibodies Directed Against *Escherichia coli* R–1 Oligosaccharide Core–Tetanus Toxoid Conjugate Bind to Smooth, Live Bacteria and Smooth Lipopolysaccharides and Attenuate Their Tumor Necrosis Factor Stimulating Activity, FEMS Immunology and Medical Microbiology 16:31–38 (1996).

Lugowski, Immunotherapy in Gram–Negative Bacterial Infections, Acta Biochimica Polnica 42:19–24 (1995).

Matthay et al., Antibody–Directed Liposomes: Comparison of Various Ligands for Association, Endocytosis, and Drug Delivery, Cancer Research 46:4904–4910 (1986).

McCabe et al, Immunization with Rough Mutants of *Salmonella minnesota*: Protective Activity of IgM and IgG Antibody to the R595 (Re Chemotype) Mutant, J. Infectious Diseases 158:291–300 (1988).

McCabe, Immunization with R Mutants of *S. minnesota* I. Protection Against Challenge with Heterologous Gram–Negative Becilli, J. Immunology 108:601–610 (1972).

McCabe et al., Cross–Reactive Antigens: Their Potential for Immunization–Induced Immunity to Gram–Negative Bacteria, J. Infectious Diseases 136:S161–166 (1977).

Miler et al., A New Polyvalent Pseudomonas Vaccine, J. Med. Microbiol. 10:19–27 (1977).

Mullan et al., Protection Against Gram–Negative Infections with Antiserum to Lipid A from *Salmonella minnesota* R595, Infection and Immunity 10:1195–1201 (1974).

Neter et al., Immunogenicity and Antigenicity of Endotoxic Lipopolysaccharides: Reversible Effects of Temperature on Immunogenicity, J. Infectious Diseases 128:56–60 (1973).

Nixdorff et al., Heterogeneity of the Haemagglutinin Responses to *Salmonella minnesota* R–Antigens in Rabbits, J. General Microbiology 71:425–440 (1972).

Nixdorff et al., Immunogical Responses to Salmonella R Antigens: The Bacterial Cell and the Protein Edestin as Carriers for R Oligosaccharide Determinants, Immunology 29:87–102 (1975).

Nnalue and Shnyra, The Lipopolysaccharide Core Domain as a Target in Immunotherapy of Sepsis, Unpublished abstract from meeting in Washington DC, Oct. 21–22, 1996.

Nnalue et al., The Disaccharide L–ά–D–Heptose 1→7–L–ά–D–Heptose 1→ of the Inner Core Domain of *Salmonella lipopolysaccharide* is Accessible to Antibody and is the Epitope of a Broadly Reactive Monoclonal Antibody, J. Immunology 149:2722–2728 (1992).

Ogert et al., Studies of the Topography of the Catalytic Site of Acetylcholinesterase Using Polyclonal and Monoclonal Antibodies, J. Neurochemistry 55:756–763 (1990).

Petrov et al., Toxicity and Immunogenicity of Neisseria Meningitidis Lipopolysaccharide Incorporated into Liposomes, Infection and Immunity 60:3897–3903 (1992).

Powers et al., In Previously Immunized Elderly Adults Inactivated Influenza A (H1N1) Virus Vaccines Induce Poor Antibody Responses that are not Enhanced by Liposome Adjuvant, Vaccine 13:1330–1335 (1995).

Poxton, Review Article: Antibodies to Lipopolysaccharide, J. Immunological Medthods 186:1–15 (1995).

Rietschel et al., Bacterial Lipopolysaccharides: Relationship of Structure and Comformation to Endotoxic Activity, Serological Specificity and Biological Function in Friedman, H., Klein T.W., Nakano, M., and Nowotny, A. (Eds.), Endotoxin, pp. 81–99, Plenum, New York (1990).

Romanowska et al., Non–typical Lipopolysaccharide Core Regions of Some *Hafnia alvei* Strains: Structural and Serological Studies, FEMS Immunology and Medical Microbiology 24:63–71 (1999).

van Rooijen et al., Liposomes in Immunology: Impairment of the Adjuvant Effect of Liposomes by Incorporation of the Adjuvant Lysolecithin and the Role of Macrophages, Immunological Communications 8:381–396 (1979).

Van Rooijen et al., Liposomes in Immunology: Evidence that Their Adjuvant Effect Results from Surface Exposition of the Antigens, Cellular Immunology 49:402–407 (1980).

Rowe et al., Structure of the Core Oligosaccharides from the Lipopolysaccharide of *Pseudomonas aeruginosa* PAC1R and its Defective Mutants, Eur. J. Biochem. 132:329–337 (1983).

Seydel et al., Structural Polymorphisms of Rough Mutant Lipopolysaccharides Rd to Ra from *Salmonella minnesota*, J. Structural Biology 110:232–243 (1993).

Shnyra et al., Role of Physical State of *Salmonella lipopolysaccharide* in Expression of Biological and Endotoxic Properties, Infection and Immunity 61:5351–5360 (1993).

Skelly et al., Stimulation of T–Independent Antibody Responses by Hapten–Lipopolysaccharides Without Repeating Polymeric Structure, Infection and Immunity 23:287–293 (1979).

Skelly et al., Immune Responses to Hapten–Lipopolysaccharide Conjugates in Mice II. Characterization of the Molecular Requirements for the Induction of Antibody Synthesis, J. Immunology 124:468–473 (1980).

Stabel et al., Comparison of Polyclonal Antibodies to Three Different Preparation of *Mycobacterium paratuberculosis* in Immunohistochemical Diagnosis of Johne's Disease in Cattle, J. Vet. Diagn. Invest. 8:469–473 (1996).

Stanislavsky et al., Specific and Non–specific Mouse Protection Induced by Different Chemotypes of the *Pseudomonas aeruginosa* lipopolysaccharides, FEMS Microbiology Immunology 105:181–190 (1992).

Stanislavsky et al., R–Form Lipopolysaccharides (LPS) of Gram–negative Bacteria as Possible Vaccine Antigens, FEMS Immunology and Medical Microbiology 18:139–145 (1997).

Stanislavsky et al., Mouse Protection Induced by *Pseudomonas aeruginosa* PAC1R and its Defective Mutants, *Salmonella minnesota* Re–Mutant and *Escherichia coli* O14, FEMS Immunology and Medicla Microbiology 11:81–86 (1995).

Stewart et al., Dependence of the Surface Expression of the Glycolipid Cerebroside Sulfate on Its Lipid Environment: Comparison of Sphingomyelin and Phosphatidylcholine, Biochemistry 29:3644–3653 (1990).

Strittmatter et al., Characterization of Protein Co–Extracted Together with LPS in *Escherichia coli, Salmonella minnesota*, and *Yersinia enterocolitica*, Microbial. Pathogenesis 2:29–36 (1987).

Svenson et al., Immunochemistry of Salmonella O–Antigens: Preparation of an Octasaccharide–Bovine Serum Albumin Immunogen Representative of Salmonella Serogroup B O–Antigen and Characterization of the Antibody Response, J. Immunology 120:1750–1757 (1978).

Suzuki et al., Direct Extraction of A and B Blood Group Antigens from Human Red Cells by Liposomes, Transfusion 36:966–968 (1996).

Swierzko et al., Specificity of Rabbit Antisera Against the Rough Lipopolysaccharide of *Salmonella minnesota* R4 (Chemotype $Rd_2P^-$), Infection and Immunity 61:3216–3221 (1993).

Tabaraie et al., Evaluation of *Salmonella porins* as a Broad Spectrum Vaccine Candidate, Microbiol. Immunol. 38:553–559 (1994).

Tan, Liposomes as Antigen Vehicles to Increase Immunogenicity: Effects of Variation of Structural Characteristics, Annals Academy of Medicine 20:78–83 (1991).

Tannock et al., Association of *Salmonella typhimurium* with, and Its Invasion of, the Ileal Mucosa in Mice, Infection and Immunity 11:365–370 (1975).

Therien et al., Liposomal Vaccine: Influence of Antigen Association on the Kinetics of the Humoral Response, Vaccine 8:558–562 (1990).

Trudel et al., Antibody Response to Rubella Virus Proteins in Different Physical Forms, Antiviral Research 2:347–354 (1982).

Van de Wijgert et al., Immunogenicity of *Streptococcus pneumoniae* Type 14 Capsular Polysaccharide: Influence of Carriers and Adjuvants on Isotype Distribution, Infection and Immunity 59:2750–2757 (1991).

Wilson et al., Evidence for Different Requirements in Physical State for the Interaction of Lipopolysaccharides with the Classical and Alternative Pathways of Complement, Eur. J. Biochem. 128:137–141 (19820.

Yasuda et al., Immunogenicity of Liposomal Model Membranes in Mice: Dependence of Phospholipid Composition, Proc. Natl. Acad. Sci. USA 74:1234–1236 (1977).

Ziegler et al., Treatment of Gram–negative Bacteremia and Shock with Human Antiserum to a Mutant *Escherichia coli*, N. Engl. J. Med. 307:1225–1230 (1982).

\* cited by examiner

|    | Lipid A | Inner core | | | Outer core | | |
|----|---------|------|-----|-----|-----|-----|-------|
| Ra | Lipid A | Kdo  | Hep | Hep | Glc | Gal | Glc   |
|    |         | Kdo  |     | Hep | Gal |     | GlcNAc |
|    |         | Kdo  |     |     |     |     |       |
| Rb | Lipid A | Kdo  | Hep | Hep | Glc | Gal | Glc   |
|    |         | Kdo  |     | Hep | Gal |     |       |
|    |         | Kdo  |     |     |     |     |       |
| Rc | Lipid A | Kdo  | Hep | Hep | Glc |     |       |
|    |         | Kdo  |     | Hep |     |     |       |
|    |         | Kdo  |     |     |     |     |       |
| Rd | Lipid A | Kdo  | Hep | Hep |     |     |       |
|    |         | Kdo  |     |     |     |     |       |
|    |         | Kdo  |     |     |     |     |       |
| Re | Lipid A | Kdo  |     |     |     |     |       |
|    |         | Kdo  |     |     |     |     |       |

FIG. 2

VACCINE AGAINST LIPOPOLYSACCHARIDE CORE

CROSS-REFERENCE TO RELATED APPLICATION

This application is a conversion of our prior U.S. provisional application, U.S. No. 60/046,680, filed May 16, 1997, which is hereby incorporated by reference.

FIELD OF THE INVENTION

This invention is in the general field of reducing the adverse effects of endotoxin from Gram-negative bacteria.

BACKGROUND OF THE INVENTION

Endotoxin (also called lipopolysaccharide [LPS]) is thought to exert many of its toxic effects following its entry into the bloodstream. The presence of endotoxin in the blood, endotoxemia, can occur in various situations, e.g., during periods of stress. For example, endotoxemia can occur in patients undergoing certain types of surgery, anticancer chemotherapy, radiation therapy, and immunosuppressive treatment, and it can also occur in patients suffering from various trauma, burns, or wounds. It occurs as well in military, police, and fire-fighting personnel as well as in endurance athletes, horses, and in livestock. It can also occur after immunosuppressive treatment, and in patients with sepsis or septic shock as well as in those suffering from stress or trauma as discussed above.

One way that endotoxin may reach the blood is from the patient's intestine because the intestine loses its ability to contain LPS during periods of infection, stress, or trauma. Normally, intestinal flora contain a large amount of endotoxin from Gram-negative microorganisms. It is estimated that the average human colon contains 25 billion nanograms of endotoxin, which is an enormous quantity when one considers that endotoxin concentrations on the order of $10^2$ are toxic to humans.

The leakage of live bacterial cells into the bloodstream can result in infection as the bacteria multiply. Many of the bacteria in the intestine are dead, and endotoxin contained within cell membrane fragments of dead bacteria can also enter the bloodstream. In this case infection per se does not develop. Instead, endotoxin from dead bacteria in the blood is thought to initiate a systemic inflammatory response by activating macrophages which release tumor necrosis factor and various interleukins. Endotoxin exposure and the resulting systemic inflammatory response can cause damage to body organs, including the lungs, kidneys, heart, blood vessels, gastrointestinal tract, blood/coagulation system, and nervous system. This proinflammatory response can be severe, causing organs to fail, sometimes resulting in death.

LPS is thought to be a major causative agent of septic shock. It is increasingly recognized that less severe forms of this systemic inflammation cause organ dysfunction as opposed to organ failure. In its mildest form, endotoxemia can cause fever, nausea, and malaise, common symptoms of patients following surgery or patients who are hospitalized for other reasons, and the symptoms even occur, for example in athletes following strenuous activity.

Greater exposure of the host to endotoxin or a greater susceptibility to its effects can result in a larger inflammatory response. For example, many post surgical patients develop pulmonary dysfunction requiring supplemental oxygen. They may also develop hematologic or renal complications. These complications often do not lead to death but instead cause suffering and increase hospital length of stay and thus health care costs. It is estimated that at least 10% of the 28 million United States surgical patients may develop systemic inflammation and possible complications as a result of exposure to endotoxin from Gram-negative microorganisms. See generally, Bennett-Guerrero et al., Crit Care Med, 25:A112, 1997 and Bennett-Guerrero et al., J. Am. Med. Ass. 277:646–650, 1997 discussing certain types of surgical patients at risk.

Among the bacteria and their respective endotoxins which are thought to commonly cause complications are *Escherichia coli, Klebsiella pneumoniae, Pseudomonas aeuruginosa*, Proteus spp., Enterobacter spp., Salmonella spp., Serratia spp, and Shigella spp. These bacteria are Gram-negative bacteria, a class characterized by a specific type of outer membrane which compromises a lipopolysaccharide (LPS) as a major constituent. Although the LPS constituent varies from one bacterial species to another, it may be generally described with reference to FIG. 1 as consisting of three structural regions: a) Lipid A; b) core; and c) O-polysaccharide outer region. The lipid region of Lipid A is embedded in the outer leaflet of the outer membrane. The oligosaccharide core region is positioned between Lipid A and the O-polysaccharide outer region. Lipid A has the same basic structure in practically all gram negative bacteria and is the main endotoxic determinant. The LPS core region shows a high degree of similarity among bacterial genera. It usually consists of a limited number of sugars. For example, the inner core region is constituted of heptose and 3-deoxy-D-manno-2-octulosonate (KDO) residues, while the outer core region comprises galactose, glucose, or N-acetyl-D-glucosamine residues displayed in various manners depending upon the strain. The O-polysaccharide outer region (also called O-specific antigen or O-specific side chain) is highly variable and is composed of one or more oligosaccharide repeating units characteristic of the serotype.

The presence of the O-polysaccharide side chain confers a smooth aspect to a culture of a wild type bacterium, and, for this reason, wild type bacteria with polysaccharide side chain are usually referred to as smooth bacteria in contrast with mutant cultures which show a rough aspect because they lack the O-polysaccharide side chain and (in some cases) part of the core region. For example, the different chemotypes of rough mutants from Salmonella are conventionally designated by the terms Ra, Rb, Rc, Rd, and Re.

As seen from FIG. 2, the LPS of each type comprises the lipid A structure. The Ra chemotype is characterized by a complete core region, the Rb chemotype is characterized by the absence of N-acetyl-D-glucosamine residues, the Rc chemotype is characterized by the absence of N-acetyl-D-glucosamine and galactose residues, the Rd chemotype is characterized by the absence of any residues constituting the outer core, and the Re chemotype is characterized by the sole KDO region attached to lipid A.

FIG. 3 is a diagrammatic representation of the five known complete core chemotypes of *E. coli* as well as the one known complete core chemotype of all Salmonella species.

Not all LPS molecules on the surface of a given cell or in a homogeneous population of cells have the same number of oligosaccharide side chains. For example, a single cell from a population of smooth strain bacteria may include some rough forms of LPS, i.e., LPS that is not substituted with any polysaccharide side chains.

Various treatments for the toxic effect of LPS have been proposed or tried. One of a mammal's defenses against endotoxemia is the presence of antibodies in the blood which can bind to and neutralize blood borne endotoxin, and immunologic methods have been proposed as an alternative or additional treatment to antibiotic therapy to prevent or control such infections or to reduce the toxic effect of endotoxin. For example, conventional polyclonal antisera and hyperimmune sera have been used in an attempt to bolster the native defenses of patients against the adverse effects of bacteria, presumably by enhancing opsonization and phagocytosis of the bacterial cells or by neutralization of the biological activity of LPS. However, the effectiveness of the antisera varies greatly depending upon a large number of factors including, for example, the composition and titer of the specific antibodies, which cannot be easily standardized. The use of these antisera may also carry a risk of transmission of viral infectious diseases.

Patients or potential donors of hyperimmune sera have been vaccinated (i.e. actively immunized) with various immunogens in an attempt to stimulate the host synthesis of cross-reactive anti-endotoxin antibodies. Various vaccine compositions and methods of immunization have been studied over the last two decades. See, e.g., Bhattacharjee A, WO 95/29662; McCabe W R, J Infec Dis 1988; 158:291; Greisman S E, Proc Soc Exp Bio Med 1978; 158:482; Goto M, Res Comm Chem Path Pharm 1992; 76:249; DeMaria A, J Infec Dis 1988; 158:301; Baumgartner J D, J Infec Dis 1991; 163:769; Cross A, J Infec Dis 1994; 170:834; Cryz S J, U.S. Pat. No. 4,755,381; Miler J M, J Med Microbiol 1977; 10:19; Ashton, F E, Microb Pathog 1989; 6:455; Dorner F, U.S. Pat. No. 4,946,677; Cryz S J, U.S. Pat. No. 4,771,127; Collins M S, U.S. Pat. No. 4,693,891; Pier G B, U.S. Pat. No. 4,285,936; Cryz S J, J Infec Dis 1991; 163:1040; Cryz S J, J Clin Invest 1987; 80:51; PCT WO92/06709; U.S. Pat. No. 5,641,492.

Vaccines should avoid the common side effects—fever, malaise, and other forms of toxicity—in the animals and humans receiving them, as reported, for example, in (Ziegler et al., New Eng. J. Med., 307:1225 (1982); DeMaria, Infec. Dis. 158:301 (1988). These side effects may be exacerbated in high risk individuals, such as pre-surgical elderly and sick patients with multiple medical problems, an important target population for the vaccine.

A study has been published in which the concentration of anti-endotoxin-core antibodies was measured in 301 patients prior to cardiac surgery and the relationship to postoperative outcome tested. Bennett-Guerrero et al. J. Am. Med. Ass. 277:646 (1997). These anti-endotoxin-core antibodies were measured using an ELISA which allegedly detects antibodies to the core of LPS. This study found that patients with a higher level of core-specific antibodies were less likely to die or have a prolonged hospital length of stay associated with complications potentially attributable to endotoxemia. This publication did not describe a method for controlling or treating endotoxemia in these patients.

Regarding the toxicity of LPS, there is some evidence that the toxicity of certain types of lipid A or LPS can be reduced in several ways.

Liposomes have been suggested as carriers for lipid A containing agents. For example, incorporation of LPS into liposomes was shown to reduce the toxicity of LPS from *Neisseria meningitidis* in an attempt to create a vaccine specific for *N. meningitides* LPS. Petrov et al., Infect. Immunity 60:3897 (1992). Other prior art showed that the incorporation of a chemically altered form of lipid A called monophosphoryl lipid A (MPLA) into liposomes resulted in reduced toxicity of the MPLA component. Richards et al. Vaccine 7:506 (1989). It appeared as if incorporating the MPLA and malaria immunogen into the liposomes resulted in an adjuvant effect, that is, incorporation into liposomes increased the immunogenicity of the malaria immunogen component of this anti-malaria vaccine.

Methods to detoxify the lipid A component of LPS have also been previously described. Bhattacharjee et al. J. Infec. Dis. 173:1157 (1996).

Genetic alteration of bacterial stains has been reported in which the resulting bacteria contain a LPS whose lipid A component causes less biological toxicity. Somerville et al., J. Clin. Invest. 97:359 (1996).

SUMMARY OF THE INVENTION

Vaccination (active immunization) with complete core rough LPS antigen particularly from *E. coli* K12 provides both strain-specific protection and cross-core protection without unacceptable toxicity or other side effects. An antigen is considered a complete-core, rough LPS in that it includes, at a minimum, Lipid A, heptose and 3-deoxy-D-manno-2-octulosonate (KDO) residues, as well as the outer core galactose and glucose residues. Typically, it also includes the outer core N-acetyl-D-glucosamine residues. For example, it includes the outer core structure of Rb and typically also the structure of Ra, as shown in FIG. 2. It does not include the O-polysaccharide outer region (also called O-polysaccharide side chain).

Thus, one aspect of the invention generally features a method of reducing the adverse effects of endotoxemia in a warm-blooded animal (a mammal, typically a human patient), by administering an effective amount of a composition comprising complete-core, rough, lipopolysaccharide (LPS) antigen (e.g., an Ra LPS) of a Gram-negative bacterium, particularly *E. coli* K12. Preferably, the immunizing composition is a cocktail of complete-core, rough, lipopolysaccharide (LPS) antigen from other Gram-negative bacterium. Useful rough LPSs are those from *E. coli* and Salmonella, particularly from each of the five known chemotypes of *E. coli*: *E. coli* R1, *E. coli* R2, *E. coli* R3, *E. coli* R4, and *E. coli* K12 (Jansson et al., Eur. J. Biochem. 115:571 (1981)). See FIG. 3. Only one core structure accounts for all known Salmonella species, and any Ra Salmonella strain can be used, for example *Salmonella minnesota* R60. Rietschel et al. Infect. Dis. Clin. N. Am. 5:753 (1991). Complete core LPS lacking polysaccharide side chains from other Gram-negative bacteria that may be useful include those from the family Enterobacteriaceae (i.e. the genera Escherichia, Salmonella, Klebsiella, Citrobacter, Shigella, Proteus, Edwardsiella, Enterobacter, Hafnia, Serratia, Providencia, Morganella, Yersinia, Erwinia), the family Pseudomonadaceae, e.g., *Pseudomonas aeruginosa* and the family Bactoroides, e.g., *B. fragilis*. See, generally, Essentials of Medical Microbiology, 31'rd Ed., Volk, et al., pp. 397 and 416 (J/P. Lippencott Co. Philadelphia, Pa. (1986) for a compilation of Gram-negative bacteria. The composition may include a complete-core, rough, LPS antigen from several (two, three, four or more) Gram-negative bacteria, each of which is different (e.g., different species or at least different strains of the same species) from the other. In such mixtures, the core antigen from each of the four bacteria may be present in functionally equal amounts (e.g., in amounts which are intended to maximize the expression of the common core epitope(s)).

Desirably, vaccines should cause the patient to produce an antibody that binds to an epitope in the core region of the LPS core of at least one Gram-negative bacterial strain whose LPS is not part of the composition, thereby providing for cross-reactivity and cross-protection. It is difficult to achieve genuine vertical and genuine horizontal cross-reactivity and cross-protection against smooth and rough gram negative LPS, in particular in *E. coli*, the species most commonly isolated from surgical and intensive care unit patients. Cross-reactivity is of two kinds, which may be described as horizontal and vertical. Vertical cross-reactivity refers to an antibody's reaction with LPS's within the same strain that are different sizes, i.e., having different degress of substitution or length of the O-specific side chain. Horizontal cross-reactivity refers to an antibody's reaction with core structures that are different—i.e., different strains, species, etc. In particular, the patient's antibody response desirably will bind and protect against smooth as well as rough forms of LPS. Without wishing to bind ourselves to any particular theory, we believe that the epitope of the immunogen used in the vaccine according to the invention is accessible in both smooth and rough forms of LPS.

It may be particularly useful to include the antigen in a liposome structure. For example, the ratio (weight:weight)of lipid in the liposome to the LPS antigen is between 1:1 and 5000:1 (more typically between 10:1 and 1000:1). The liposome may include a component to provide stability or alter the compound's charge, selected from the group consisting of: phospholipid, cholesterol, positively charged compounds, negatively charged compounds, amphipathic compounds. Multilamellar type liposomes (MLV) in particular may be used. Small or large unilamellar liposomes (SUVs and LUVs) also may be used.

The composition may be administered intramuscularly intravenously, subcutaneously, intraperitonealy, via the respiratory tract, or via gastrointestinal tract. The dose of antigen can be readily determined by standard dosage trials which correlate dosage with titer and/or protection. A functional dosage may be between 0.01 ng and 1000 ng per kilogram of patient body weight, but further optimization may indicate that higher dosages (up to 100 µg/kg of body weight) are desirable consistent with safety and avoiding untoward side effects. IgM antibodies can provide suitable protection, and, were the goal is generation of IgM antibodies, the composition may be administered sufficiently in advance to permit IgM antibodies to be produced (at least 2 days more typically longer) prior to potential endotoxin exposure. Also in that case, the composition would not be administered so far in advance that the IgM response deteriorates substantially—e.g., less than 14 days prior to exposure. The composition may be administered in multiple doses, the first of which is administered at least 2 days prior to potential endotoxin exposure.

Antigen in the composition may be present as part of bacteria that have been killed e.g., by heat or formaldehyde. Alternatively, the antigen may be separated from the bacterium before formulation of the composition. Alternatively the LPS antigen can be in the form of purified LPS or complexed to an acceptable carrier. Appelmelk et al., J. Immunol. Meth., 82:199 (1985).

The antigen may be chemically detoxified. The bacterium may be genetically engineered for various reasons, e.g., to reduce toxicity. The composition may also include an adjuvant, e.g., alum.

The invention also features vaccine compositions described above in connection with the method. Thus, the vaccine is comprised of an effective amount of one or more complete-core, rough, LPS of a Gram negative bacteria. Upon administration to a warm-blooded animal the compositions stimulate the synthesis of antibodies which recognize an epitope in the core region of the LPS molecule and which are cross-protective against endotoxemia caused by at least two different Gram-negative bacterial strains having different core structures. In particular, the antibodies synthesized in response to the vaccine are cross-protective against smooth LPS as well as complete core rough LPS (lacking O-polysaccharide side chains). In *E. coli*, the antibodies induced by the vaccine preferably react with all common smooth strain isolates, and preferably also with rough forms of all five core types (R1, R2, R3, R4, and K12). Preferably the antibodies induced by the vaccine are also reactive with both smooth and rough forms of LPS of different strains of Salmonella.

Furthermore, the vaccine described in this invention preferably causes no unacceptable toxicity following its administration to mammals. Toxicity may be controlled by incorporating the LPS into liposomes, by detoxifying the LPSs lipid A component and/or by alteration of the lipid A component by genetic manipulation of the above mentioned bacterial strains.

The vaccine composition can be used to immunize a donor, from whom antibodies are harvested for administration to a patient. Preferably the antibodies harvested comprise a substantial percentage of IgM class antibody.

Another aspect of the invention features a method of quantitating lipopolysaccharide incorporated into liposomes (PAS method). This method, unlike e.g., typical radiolabelling methods, does not require conversion of the lipopolysaccharide to a form which is unsuitable for clinical use.

Other features and embodiments of the invention will be apparent from the following description of specific embodiments.

BRIEF DESCRIPTION OF THE DRAWINGS

FIG. 2 is a diagrammatic representation of the chemical structure of Salmonella R-mutants.

DESCRIPTION OF THE PREFERRED EMBODIMENTS

Medical Indications

Figure 1:
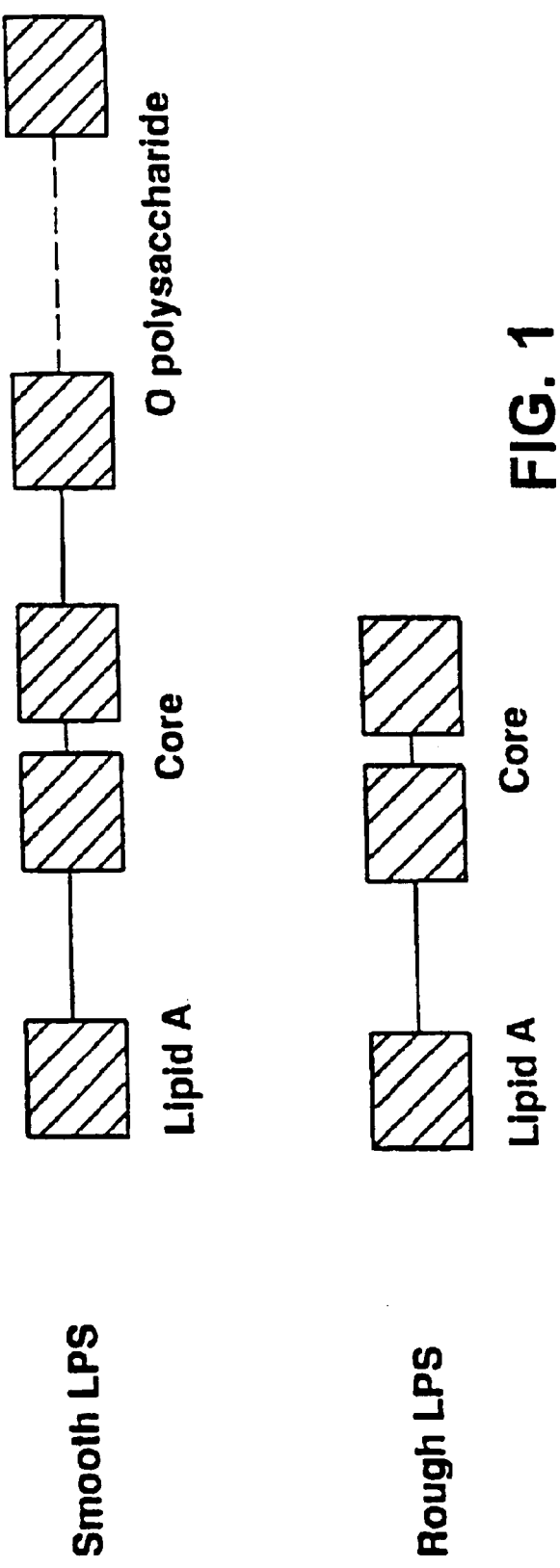
FIG. 1 is a diagrammatic representation of smooth and rough LPS.
Figure 3:
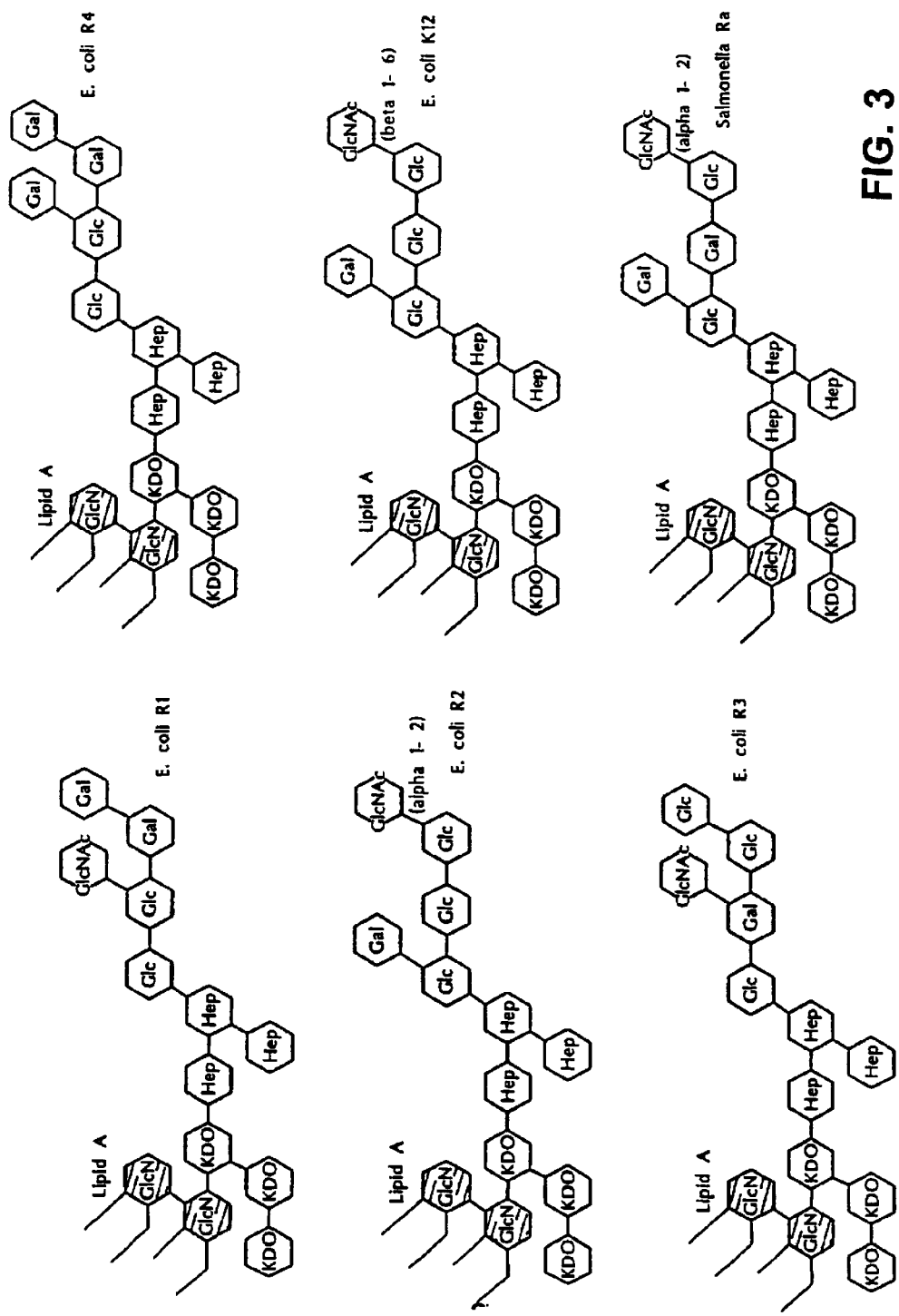
FIG. 3 is a diagrammatic representation of the chemical structure of known core types found in Salmonella and Escherichia complete core rough LPS.

The patients to be treated with the vaccine include those at risk for endotoxin exposure. Specific candidates for active immunization include patients scheduled for surgery, patients subjected to chemotherapy or radiation therapy as well as burn patients, trauma patients, dialysis patients and hospitalized (particularly ICU) patients, whether or not they exhibit sepsis or septic shock. Other potential candidates for vaccination include members of the military, fireman, and policeman, as well as endurance athletes and livestock such as horses or cows.

LPS Component

As described above, the LPS antigen to be included in the vaccine can be any complete core LPS lacking O-polysaccharide side chains, preferably from *E. coli* K12, as described below. Although Rb chemotypes may be used, the preferred embodiment is Ra or complete core chemotypes. LPS can be purified from cultured bacteria or purchased commercially, e.g., from Difco, Sigma, List Biologicals, in Campbell, Calif. The organisms in question are widely available from depositories, including the National Culture Type Collection in England (NCTC); the University of Edinburgh collection in Edinburgh Scotland,[1] and the Forschungsinstitut in Borstell (FB), Germany D-2061. Examples of specific bacterial include, but are not limited to, the following strains: *E. coli* K12—e.g., Edinburgh #MPRL2320; FB W3100 or List Biologicals; *E. coli* R1—e.g.Edinburgh #MPRL2316 or FB F470; *E. coli* R2—e.g., Edinburgh #MPRL2317 or FB F576; *E. coli* R3—e.g., Edinburgh #MPRL2318 or FB F653; *E. coli* R4—e.g., Edinburgh #MPRL2431 or FB F2513; Ra *S. minnesota* R60 Edinburgh #MPRL1265 or List Biologicals; *S. typhimurium* Ra (e.g. TV119,1542), *P. aeruginosa* PAC611 (e.g., Edinburgh #MPRL1091) and *K. aerogenes* M10B (e.g., Edinburgh #MPRL0954), *S. minnesota* Rb chemotype (e.g. Edinburgh #MPRL1091) R345); *Bacteroides fragilis*—NCTC 9343; *B. vulgatis* NCTC 10583; *B. thetaiotaomicron* NCTC 10582.

[1] University of Edinburgh Medical School (Edinburgh, 3Scotland), attention Ian Poxton, Ph.D.

Without wishing to bind ourselves to a single theory by which the invention operates, we note that the inner core region may contain an important epitope in terms of stimulating the synthesis of cross-reactive and cross-protective anti-LPS antibodies. However, sufficient outer core structures may be necessary to maintain the inner core epitope in a three-dimensional structure which is similar to that encountered in clinically significant LPS isolates (i.e. smooth and rough forms of complete core LPS). The absence of polysaccharide side chain (i.e. rough LPS) allows the core epitope to be the dominant epitope. In smooth forms of LPS, the polysaccharide side chain is a much more dominant epitope than the core thus significantly reducing the relative amount of anti-core antibody produced. In other words, vaccines containing smooth LPS elicit primarily a serotype specific (i.e. anti-polysaccharide side chain) antibody response as opposed to the anti-core response which is the focus of our invention.

*E. coli* K12 may be particularly useful because it is not generally present in the patient population. Therefore, K12 is less likely to provoke a memory response to the outer core, and more likely to provoke a cross-reactive memory response to the inner core.

If whole bacteria are to be included in the vaccine the bacterium will be killed by a technique well known to those in the art, such as heat killing or formaldehyde killing. In this case, the entire LPS of rough mutant bacterium will be included as part of the killed bacterium. It is desirable to avoid bacterial killing methods which can alter the core.

Alternatively, complete core LPS can be isolated from the desired bacteria according to standard techniques as outlined by Hancock et al., Bacterial Cell Surface Techniques, pp. 91 (John Wiley & Sons 1988). As noted, it is preferable to include all of the core LPS, without the O-polysaccharide outer LPS structures, i.e. use R-mutant bacteria expressing full LPS core.

Patient Response

As noted, the desired patient response is cross-protective antibodies that bind to the core of rough and smooth LPS of Gram-negative bacteria generally, regardless of whether their outer LPS structures are similar.

For example, in *E. coli*, the antibodies induced by this vaccine preferably react with all common smooth strain isolates, and preferably also with rough strain LPSs of all five core types (R1, R2, R3, R4, and K12). Preferably the antibodies induced by this vaccine are also reactive with different smooth and rough LPSs of Salmonella.

It is possible to achieve a vigorous and effective antibody response using compositions with acceptable levels of (or no) toxicity. The vaccine stimulates the synthesis of antibodies which recognize an epitope in the core region of the LPS molecule and which are cross-protective against endotoxemia caused by at least two different Gram-negative bacterial strains having different LPS structures and in particular are cross-protective against smooth strains as well as complete core rough strains.

Typically, the vaccine will be a cocktail of the purified LPS from different strains of bacteria, preferably rough strains having a complete core, for example a mixture of LPS from K12 with LPS from R1 and R3 rough strains of *E. coli*, or with the Ra strain of *Salmonella minnesota* R60. *E. coli* R2 and R4 are less important but also candidates. Preferred cocktails (depending on the breadth of protection desired) include K12 with R1; K12 with Pseudomonas (e.g., *P. aeruginosa*) and Klebsiella (e.g., *K. aerogenes*). Since the Bacteroides are a particularly significant population in the gut, it may be important to protect specifically against Bacteroides endotoxin by including Bactoeroides in the cocktail. e.g., together with K12 or together with K12, Pseudomonas and Klebsiella.

Alternatively, the purified LPS from one of these strains, a mixture of any combination of these strains, or a different strain of bacteria may be used in any ratio of the individual strains in the case of use of more than one LPS type.

The route of administration is preferably subcutaneous or intramuscular, although any alternative route which results in these immunogens reaching the antigen presenting cells and antibody producing cells is acceptable. Some other examples include but are not limited to intravenous, intraperitoneal, and via the respiratory or gastrointestinal tract.

The dose of this composition should stimulate the host to produce increased quantities of cross-reactive and cross-protective antibodies levels, consistent with avoiding toxicity, as described above.

The composition is administered before endotoxin exposure. To the extent that the vaccine works in part by stimulating the host to synthesize antibodies of the IgM class, the vaccine is preferably given between 2 to 14 days prior to potential endotoxin exposure. Alternatively, additional doses of any of the possible permutations of this vaccine may allow for greater effectiveness and increases in desired antibody levels or even further reduced toxicity. It is anticipated that in most vaccinees the antibody response to inner core determinants will be a secondary (i.e. memory) response as opposed to a primary (i.e. naive) response. This is because most vaccinees will have been exposed at some time in their lifetime to the LPS core epitopes, presumably from LPS that has leaked through the gut barrier into the bloodstream. In other words, an important function of our method of vaccination is to cause an increase in the serum concentration of antibodies which may already be present, but at levels which do not allow for sufficient protection from a toxic exposure of LPS during periods of stress and trauma. The above in no means suggests that there are not patients who will also benefit from vaccination with this invention by means of a primary (i.e. naive) antibody response.

A vaccine with the LPS mentioned above is preferably rendered non-pyrogenic and non-toxic by incorporation of the LPS into liposomes. The liposome (exclusive of the LPS component) may contain a combination of (1) a phospholipid and cholesterol or (2) a phospholipid, cholesterol and a negatively or positively charged (lipophilic) amphipathic compound. The phospholipid component may be selected from the group comprising any lipid capable of forming liposomes, including, but not limited to: any phosphatidylcholine derivative, glycerophosphatides, lysophosphatides, sphingomyelins, and mixtures thereof. The negatively charged (lipophilic) amphipathic compounds may be selected from the group comprising di(alkyl)phosphates, phosphatidic acid, phosphatidylserine, phosphatidylglycerol, phosphatidylinositol, dicetyl phosphate, or any other similar negatively charged amphipathic compound that can impart a negative charge to a liposome surface. When positively charged (lipophilic) amphipathic compounds are employed; they are selected from the group comprising alkyl amines, such as stearylamine and hexadecylamine. The ratio in the constituents of the liposomes (exclusive of the LPS) will effect the liposomes' charge, rigidity, stability and may vary greatly while still allowing for reduced toxicity and increased immunogenicity of the LPS they contain. Polyethylene glycol lipids (PEG) may be incorporated into the liposomes, for example at approximately 10 to 20 mole %, in order to increase the amount of time that the liposomes remain in the systemic circulation, thus affecting their immunogenicity. Alternatively, very rigid bilayers may be made by using lipids which are gel phase at body temperature (37 degrees C.), for example distearoyl phosphatidylcholine or distearoyl phosphatidylserine. The type of liposomes used is preferably multilamellar liposomes (MLV) but alternatively upon sonication, or by alternative methods of manufacture, small or large unilamellar liposomes (SUVs and LUVs) of varying sizes can be employed. Different salt forms of LPS may alter the degree of incorporation of LPS into the liposomes, for example, the acid salt form, magnesium salt form, and calcium salt form may allow for increased incorporation due to their increased hydrophobicity.

Liposomes are defined as closed vesicles, or sacs, which contain phospholipids (examples of which are lecithin and sphingomyelin) and which may contain other lipids (examples of which are cholesterol and other steroids; charged lipids such as dicetyl phosphate and octadecylamine; glycolipids; fatty acids and other long-chain alkyl compounds; hydrophobic glycoproteins; and lipid soluble vitamins and lipoidal surfactant-like molecules). When shaken in the presence of an excess amount of water, the lipid mixture is formed into discrete particles consisting of concentric spherical shells of lipid bilayer membranes which are referred to as multilamellar liposomes (MLV). Upon sonication, or by alternative methods of manufacture, small or large unilamellar liposomes (SUV or LUV, respectively) can be formed.

Upon injection into animals and man, liposomes are taken up rapidly by cells of the reticuloendothelial system, particularly those of the liver. Because of the relative impermeability of liposomes and their speedy removal from the circulatory system, substances such as lipid A and certain forms of LPS remain incorporated within the liposomes and are less likely to be exposed to cells and/or receptors through which they can exert potentially toxic effects. Moreover, liposomes may allow for a prolonged effectiveness through slow biodegradation of the multilamellar membrane structure of the liposomes.

The toxicity of the lipid A component of the above mentioned complete core rough mutant strains also can be reduced or eliminated by chemical detoxification as described in Bhattacharjee A et al., WO 95/29662. The preferred method for this detoxification maintains the LPS configuration such that it still stimulates the synthesis of antibody/ies which recognize an epitope in the core region of the LPS molecule and which is cross-protective against endotoxemia caused by at least two different Gram-negative bacterial strains having different core structures. In particular, the antibodies synthesized in response to this vaccine are cross-protective against smooth strains as well as complete core strains. The detoxified LPS may be administered in the form of purified LPS, or alternatively can be incorporated into liposomes or complexed to an acceptable carrier.

Alternatively the toxicity of the lipid A component of the above mentioned strains of bacteria can be reduced or eliminated by genetic alteration of the bacterial strains as described in Somerville J E et al, J Clin Invest 1996; 97:359–365. The resulting LPS from these cells (in the form of heat killed cells) is reduced in toxicity while still affording immunogenicity to LPS core. The preferred method for this genetic alteration maintains the LPS in a sufficient three-dimensional shape that it still acts sufficiently as an immunogen in a host to stimulate the synthesis of antibody/ies which recognize an epitope in the core region of the LPS molecule and which is cross-protective against endotoxemia caused by at least two different Gram-negative bacterial strains having different core structures. In particular, the antibodies synthesized in response to this vaccine are cross-protective against smooth strains as well as complete core rough strains. At the same time, this genetic process preferably renders the LPS non-pyrogenic and non-toxic in the warm-blooded animal. The LPS from these genetically altered bacterial strains are preferably administered in form of purified LPS incorporated into liposomes. LPS from these altered strains can alternatively be administered in the form of killed cells. Alternatively, the detoxified LPS may be administered in the form of purified LPS, or alternatively can be complexed to an acceptable carrier.

Toxicity of any of the LPS rough antigen compositions described in this invention may also be reduced by other methods, for example, competitive detoxification of lipid A by synthetic anti-endotoxin peptides. Rustici et al. Science 259:361 (1993). An alternative method of reducing toxicity is to administer the LPS antigen with or at around the same time as an anti-inflammatory agent, e.g., anti-TNF-alpha monoclonal antibody. Fisher C J et al. N Engl J Med 334:1697 (1996).

EXAMPLES

Examples herein offered to illustrate the invention are not intended to limit the scope thereof. These examples are offered to indicate experiments that may be done, with no implication that all or any of the experiments have in fact been performed.

Materials for Liposome Preparation

Synthetic dimyristoyl phosphatidyl choline (DMPC), dimyristoyl phosphatidyl serine, and dimyristoyl phosphatidyl glycerol (DMPG) were purchased from Avanti Polar Lipids. Cholesterol, 3-(N- Morpholino) propane sulfonic acid (MOPS), periodic acid, and pararosaniline based Schiff's reagent are purchased from Sigma. Sterile saline and water for irrigation are purchased from Abbott labs. 3M Empore solid phase extraction discs are obtained from Fisher. Limulus amebocyte lysate (LAL) standards and reagents are obtained from Associates of Cape Cod.

Materials and reagents are depyrogenated in one or more of the following procedures: 1) Heating—glassware are heated to approximately 180 degrees for no less than 16 hr; 2) Base Treatment—immersed in isopropanol/concentrated potassium hydroxide for not less than 2 hours; 3) Hydrogen Peroxide—immersed in concentrated hydrogen peroxide for not less than 1 hour at 70 degrees Celsius then rinsed with depyrogenated water; 4) Ultrafiltration—solutions are filtered through Amicon centriprep ultrafiltration membranes (3000 M.W.).

All glassware, plasticware, solutions, and buffers are free of contaminating endotoxin and verified by use of the standard LAL assay (Pyrotell and Pyrochrome from Associates of Cape Cod, Cape Cod, Mass., USA).

MOPS Saline Buffer and 0.5% periodic acid solutions are stored at room temperature prior to use. Lipid stock solutions are stored at −20 degrees Celsius. LPS is stored dissolved in water for irrigation or in 0.1% TEA in glass or polystyrene containers (Evergreen) at 4 degrees Celsius. Liposome preparations are stored at 4 degrees Celsius. Pararosaniline based Schiff's reagent is stored at 4 degrees Celsius prior to use.

Methods

Lipopolysaccharide

Established strains of the following bacteria are maintained according to standard procedures: K12, R1, R2, R3, and R4 rough strains of *E. coli*, *E. coli* smooth strains O18, 06, 0157, 012, 015, and the Ra strain of *Salmonella Minnesota* R60 can be obtained as described above. Smooth and rough LPS are purified according to the established method described in Hancock et al., cited above, pp 91–92. LPS from *E. coli* J5 (Rc chemotype), *E. coli*, *S. Minnesota* R595 (Re chemotype), and *S. Minnesota* (wild type), and *S. typhimurium* (wild type) can be obtained from List Biological Laboratories Inc. (Campbell, Calif.). Native LPS may be used as well as acid form (deionized) LPS made by electrodialyzing the native LPS using the established method described in Hancock et al. cited above at 93–95.

Incorporation of LPS into Liposomes

Liposomes are prepared by standard procedures. Multilamellar vesicles (MLV) are prepared according to the method of Dijkstra et al, J Immunol Methods 1988; 114:197–205, with some modifications, as indicated in Methods #1 and #3, below, or a novel method (method #2).

For example, in method #1, 1 ml of 5 mg/ml of native *E. coli* K12 (Ra) LPS in water was added to a 1 ml aqueous dispersion of 50 mg lipid (DMPC:DMPG:cholesterol, 4:1:4, mol/mol), i.e. a lipid:LPS ratio of 10:1 (wt/wt). The combined solution was then probe sonicated at 40–50 degrees Celsius for five 2 minute periods with 2 minute wait periods in between each sonication. The solution was then rotovapped to dryness and resuspended in a buffer consisting of 4 mM MOPS, 153 mM NaCL, ph 7.8. LPS not incorporated into the liposomes (free LPS) was removed by centrifuging the preparation 3 times at 10,000 rpm in a Komp Spin KA 21.5 rotor for 10 minutes, decanting all supernatant, and resuspending the pellet in the original volume of buffer. This procedure was repeated 3 times and reduced the concentration of unincorporated LPS significantly. This method for reducing free LPS can be used following most liposome preparation methods.

In method #2, a solution of 5 ml chloroform:methanol (2:1, v/v) was vortexed together with 2 ml of 0.1 M HCl. The lower organic phase was then allowed to separate from the upper, removed, and used to dissolve 5 mg of acid form LPS. 50 mg of lipid (DMPC:DMPG:cholesterol, 4:1:4, mol/mol) was then dissolved in the LPS solution. The solution of codisolved LPS and lipid was rotovapped to dryness, and resuspended as in method #1.

In method #3, briefly, a 1 ml of a lipid stock solution consisting of 4 mM dimyristoyl phosphatidyl choline:1 mM dimyristoyl phosphatidyl serine: 4 mM cholesterol was rotovapped to dryness at 50 degrees Celsius. 50 µl of a 0.1 mg/ml solution of mixed LPS consisting of equal weights of LPS from *Escherichia coli* strains K12, R1, R2, R3, R4 and *Salmonella minnesota* R60 suspended in 0.1% TEA is added with 150 µl of water. The preparation was then vigorously vortexed and sonicated for not less than 5 minutes in a bath type sonicator with hot tap water in the bath. The preparations were then rotovapped (or lyophilized) to dryness again and resuspended in a buffer consisting of 4 mM MOPS 153 mm saline pH 7.8 with vigorous vortexing.

In some of the methods of incorporation of LPS into liposomes a single LPS type was used (e.g. 5 mg of *E. coli* K12 (Ra)) while in others, equal amounts of different LPSs were used (e.g. 0.83 mg of LPS from 6 complete core rough mutants).

Large unilamellar vesicles (LUV) were prepared from MLV by repeated (minimum of 15) passages through a depyrogenated pair of 100 nm polycarbonate membranes housed in an Avestin Liposofast extruder which was also depyrogenated prior to use by the hydrogen peroxide treatment above.

LPS incorporated into liposomes from method #3 was purified on a 1.1×28.5 cm BioGel A15M column using 4 mM MOPS/153 mM saline as the running buffer and 0.7 ml/min as the flow rate. This step maybe unnecessary since there was no difference in the lymulate ameoba lysate (LAL) activity between purified and unpurified liposomes due to the almost complete (>99.9%) incorporation of the free LPS into the liposomes.

In vitro Quantitation of Toxicity of LPS

Quantitation of the biological activity of the toxic lipid A component of all samples of vaccine and controls was accomplished using the standard LAL assay according to the manufacturer's instructions. (Pyrotell and Pyrochrome from Associates of Cape Cod, Cape Cod, Mass., USA). The rate of incorporation of free LPS into liposomes is generally reflected by a significant decrease of LAL activity following effective incorporation. Rates of incorporation of LPS into liposomes using traditional methods, including those described above, usually exceed 90% and in some of the methods exceeded 99%.

Periodic Acid/Schiff's Base (PAS) Stain for LPS

Aliquots of LPS containing either MLV or LUV are diluted to 2 ml with water and extracted with 2 ml toluene. After vortexing and a 5 minute 2800 rpm centrifugation in a Sorvall GLC-2 centrifuge, the upper toluene phase is removed and the aqueous phase is reextracted with 2 ml of fresh toluene. The aqueous phase and interphase are then taken, acidified with 30–50 µl of concentrated hydrochloric acid and extracted with 5 ml of chloroform:methanol (2:1). The aqueous phase is reextracted once with chloroform and the combined organic phases are dried under nitrogen at 50–60 degrees Celsius. Residues are then dissolved in chloroform:methanol (2:1) and spotted on an Empore C8 extraction disc alongside an LPS standard curve spotted from 50% ethanol. Discs are dried in vacuo and incubated in 0.5% periodic acid at room temperature for approximately 30 minutes. They are then removed, rinsed with distilled water, and placed in capped test tubes containing pararosaniline based Schiff's reagent. The tubes are then warmed under hot tap water until color develops. The discs are then removed, rinsed again, and dried. Quantitation of the resulting spots is done on an Agfa Arcus II desktop scanner in conjunction with Adobe Photoshop and NIH Image software.

Immunization and Pyrogenicity Testing

The pyrogenicity and toxicity of a vaccine comprised of LPS is best measured in the rabbit model of pyrogenicity established and outlined in the United States Pharmacopiae.

(USP 23, <151>, 1995, Rockville, Md.) In this established protocol, if an experimental substance is administered and does not cause pyrogenicity in rabbits relative to control animals, that substance is defined as being non-pyrogenic and is unlikely to cause fever or toxicity in other mammals, particularly humans, following its administration. This protocol is an ideal model since rabbits and humans are similarly sensitive to endotoxin.

Briefly, mature female New Zealand White rabbits between 1.8 and 3.0 kg were sham tested twice to insure their suitability for pyrogenicity testing. All testing materials were administered as specified, either intravenously (IV) as a 1 ml volume or intramuscularly (IM) as a 0.6 ml volume. Three rabbits are used per group as necessary for tests completed to comply with regulatory requirements. However, 2 rabbits per group were sufficient to demonstrate large differences in pyrogenicity between free LPS and LPS incorporated within liposomes in examples described below. Temperatures of the rabbits were measured to insure a steady baseline and following administration of the test sample were monitored at 15 minute intervals for 3 hours. A material is considered non-pyrogenic if no rabbit shows an individual rise in temperature of >0.5 degrees C. above baseline.

Measures of Efficacy of Various Immunogens

A well recognized test for the effectiveness of an immunogen is to administer the immunogen to a warm blooded animal, typically a rabbit or a human subject, and then withdraw blood samples periodically for the determination of antibody levels. Blood samples were drawn from a marginal ear vein into a red top tube the day before testing and at different time points following intramuscular (thigh muscle) immunization. Some intramuscular immunizations were performed with the administration of the adjuvant Alum. In these cases 0.3 ml(equal to 1.50 mg) of Alum (Alhydrogel 0.5% diluted from stock 2%, Sergeant Co., Clifton, N.J.) was mixed thoroughly with 0.3 ml of vaccine immunogen prior to administration. Blood was centrifuged, the serum removed, and stored at −80 degrees C.

Binding of Immunized Rabbit Serum to LPS by ELISA

The cross-reactivity of sera from the immunized rabbits was determined by a standard method of binding of sera to purified LPS in enzyme-linked immunosorbent assay (ELISA). Sera was obtained from rabbits before and after immunization with different possible immunogens. This sera was tested against numerous purified LPS in order to determine the degree of horizontal cross-reactivity and vertical cross-reactivity of the sera. The rabbit serum following the method of active immunization described in this invention bound to smooth and complete core rough LPS of *Escherichia coli* as well as smooth and complete core rough LPS of Salmonella. It demonstrated superior binding than sera from rabbits immunized with immunogens from prior art such as the extensively tested Rc J5 mutant of *Escherichia coli*, the Re mutant of *Salmonella Minnesota*, and lipid A.

LPS-polymyxin Complexes

LPS molecular weights were calculated as described previously (Scott B B et al., Serodiag Immunother Infect Dis; 4:25(1990)). Purified LPS at 0.2 mM in pyrogen-free water (5 ml) were mixed with polymyxin B sulphate (Sigma) at 0.4 mM in pyrogen free water (5 ml), and sonicated together with approximately ten short (5 second) bursts of sonication. The resulting milky suspension was placed in a 2000 MWCO membrane and dialysed overnight against freshly-distilled water containing 0.05% Na axide (w/v) to remove excess uncomplexed polymyxin B. The dialysed material, often presenting as a flocular precipitate, was recovered as a 10 ml suspension with a presumptive LPS concentration of 0.1 mM, and stored in polypropylene Minisorb tubes (Nunc) at −40 C.

LPS Coating on Microplates

LPS-polymyxin complexes were resuspended with sonication. LPS-polymyxin complexes were diluted 1:80 in 0.05 M carbonate-bicarbonate buffer pH 9.6, containing 0.05% sodium azide, which had been freshly prepared using freshly-distilled water. The diluted complexes (containing 1.25 micromolar LPS) were maintained in even distribution in coating buffer by continuous rapid stirring, and added at 100 microliters per well to 96-well microtiter plates or 8-well microtiter strips (in 96-well frames). The microtiter plates and strips used were ELISA-grade polystyrene (Greiner, medium-binding grade, flat-bottom wells): some other grades and some other manufacturers microtiter plates may be unsuitable for this assay. Plates were stacked, wrapped in plastic (Clingfilm), and incubated overnight at 37 C. The plates were washed as previously described using phosphate-buffered saline (PBS) with 0.05% (v/v) tween-20. A 5% solution of bovine serum albumin (BSA) in PBS, containing 0.05% sodium azide, was added at 120 microliters per well. The plates were stacked, wrapped in plastic, and incubated overnight at 37 C. The plates were washed as before, rinsed using freshly-distilled water, blotted by inverting on absorbent paper, and dried at 37 C. The dried plates were sealed in plastic bags (one plate per bag) and stored at −40 C. until used.

LPS ELISA

Samples of test serum or plasma were diluted 1:200 in ELISA diluent [PBS/tween-20 (0.05% v/v)/polyethyleneglycol 8000 (4% w/v)/BSA (1.0% w/v)/sodium azide (0.05% w/v)], and added at 100 microliters per well, in triplicate, to LPS-coated plates. Plates were incubated at 37 C. for 5 hours in a still-air (no fan) incubator, then washed (PBS/tween). Other dilutions, incubation durations, and test replication may be used, however, for any given set of experimental control and experimental groups should be subjected to identical conditions. An alkaline-phosphatase-conjugated species-specific, immunoglobulin heavy-chain-specific antibody was used to determine the amount of each immunoglobulin class bound. IgM antibodies were determined with mu-chain specific conjugates and IgG antibodies were determined with gamma-chain specific conjugates. Heavy-chain specific species specific antibodies (e.g. anti-rabbit Ig antibodies purchased from Harlan Sera-Lab (UK), were used at 1:1000 in ELISA dilution buffer. The diluted conjugates were added at 100 microliters per well, and plates were incubated for 120 minutes at 37 C. The plates were washed in PBS/tween, rinsed in distilled water, blotted, and 100 microliters of freshly-prepared pNPP alkaline phosphatase substrate solution (Sigma N-2770) was added per well. The color was allowed to develop for 30 minutes at room temperature, and plates were read (at 405 nm and reference at 650 nm) on an automated ELISA plate reader (Molecular Devices Thermo-max) and tests were expressed as the net optical density at 405 nm and 650 nm (reference). Alternatively, test results can be read as above and expressed as a percentage of a standard on the same plate using automated curve fitting from device-related software (Molecular Devices Softmax). Test samples can be compared to a laboratory standard imuune serum from the same species, placed as a triplicate series of 8 doubling dilutions in ELISA diluent (standard curve) from, say, 1:50, down one column of triplicate wells on each microplate.

Binding of Immunized Rabbit Serum to LPS by Western Blotting

The cross-reactivity of sera from the immunized rabbits was also determined by the standard method of binding of sera to purified LPS in Western blotting. Sera was obtained from rabbits before and after immunization with different possible immunogens. This sera was tested against numerous purified LPS in order to determine the degree of horizontal cross-reactivity and vertical cross-reactivity of the sera. The rabbit serum following active immunization with the method of active immunization described in this invention bound to smooth and complete core rough LPS of *Escherichia coli* as well as smooth and complete core rough LPS of Salmonella. It demonstrated superior binding than sera from rabbits immunized with immunogens from prior art such as the extensively tested Rc J5 mutant of *Escherichia coli* and is expected to demonstrate superior binding compared with serum from rabbits immunized with purified lipid A as well as rabbits immunized with LPS from the Re mutant of *Salmonella minnesota*.

PAGE analysis was performed on 12% (w/v) acylamide gels with the buffer system of Laemmli (Nature; 227:680–85 (1990)),except SDS was omitted from the stacking and separating gel buffers. Samples of LPS (5–10 micrograms for rough LPS and 20–25 micrograms for smooth LPS, mixed with Laemmli's sample buffer) were loaded onto the gel and electrophoresed at 60 volts until the sample had entered the separating gel, and then at 150 volts until the dye front had migrated 7.5 cm through the gel. The separated LPS was stained by the modified silver stain of Hancock and Poxton (Bacterial Cell Surface Techniques, pub. Wiley, p. 281 (1988)) except that oxidation was done for 15 minutes. For immunoblotting, the LPS was transferred to nitrocellulose membrane (Schleicher and Schuell, Germany), 0.2 micrometer pore size at 10–12 volts for 16 hours at 4 degrees Celsius with the Tris, glycine, methanol buffer of Towbin et al, Proc Natl Acad Sci USA; 76:4350–54 (1979)). The transferred LPS was immunostained as described in Hancock and Poxton (Bacterial Cell Surface Techniques, pub. Wiley, p. 204–5 (1988)), except that incubation times and serum dilutions were selected to give best results, and the immunoblot was rinsed prior to developing.

The LPS content extracted from a smooth bacterium was separated by electrophoresis into bands corresponding to LPS molecules having different molecular weights, depending on the size of the O-specific side chain. These LPS molecules ranged from LPS molecules without any O-specific side chain (equivalent to the size of a complete core (Ra) rough mutant) to LPS molecules having 40 or more units in the side chain.

Protection Based on Inhibition of LPS Induced Stimulation of the LAL Assay by Serum from Vaccinated Rabbits The limulus amebocyte lysate (LAL) assay is an established test for the biologic activity/toxicity of lipid A (the toxic component of LPS). This assay quantitates the activity of a biologically active LPS, whereas in the presence of protective anti-LPS antibodies there is significant inhibition of the LAL test due to competitive binding and neutralization of the LPS. There are numerous methods for using the LAL assay to demonstrate protection from anti-LPS antibodies. LAL test kits can be purchased from manufacturers, e.g. Coatest Endotoxin from Chromogenix, Sweden. Different versions of the LAL assay can be used, e.g. gel-clot version or chromogenic version.

In an example of this method, a kinetic chromogenic LAL assay was used. In this assay, serum was obtained from a rabbit before and after vaccination with complete core LPS incorporated into liposomes. *E. coli* R1 LPS (1000 micrograms/ml) was diluted ⅕ into pyrogen-free water on a microplate, then five-fold diluted across the plate, allowing for a final volume of 40 ul in 5 wells (1000 ug/ml to 1.6 ug/ml). Dilutions of LPS are performed to avoid: 1) having only wells in which there is not enough LPS to cause LAL activation in the presence of serum; 2) having only wells in which there is an excessive amount of LPS. There was a dilution series for each serum or control to be tested (total 3 rows).

Row A—pyrogen-free water row B—day-0 rabbit serum (complete core immunogen)

Row C—day-63 rabbit serum (complete core immunogen)

20 ul of water or rabbit serum was added to each well and left for 30 minutes at room temperature. 20 ul of LAL/substrate was then added using a multi-tip pipettor (start of reaction) to each well, placed immediately in reader, and read at 20 sec intervals for 120 minutes. The time (seconds) from start of reaction to an optical density (OD) of 0.5 is a reflection of the degree/speed of LAL activation. In the presence of water and LPS, the LAL reaction proceeded quickly and an OD of 0.5 was reached quickly. Pre-immunization serum contains some anti-LPS antibodies as well as non-specific inhibitors of LPS (e.g. lipoproteins). This serum partially neutralized the LPS thus slowing down the LAL reaction and increasing the time required for the OD to reach 0.5. Post-immunization serum from the complete-core immunized rabbit resulted in a significant neutralization/protection of the R1 LPS as evidenced by the marked prolongation of the time required to reach an OD of 0.5. Similar results were obtained using other types of stimulating LPSs and were consistent with the ELISA LPS binding data described earlier.

In another method using inhibition of LAL activity, a known quantity of LPS is added to several dilutions of serum from both pre- and post-vaccinated subjects and the LAL activity (EU) for each is compared. Protective anti-LPS antibodies in serum, in particular the post-vaccination serum, result in lower LAL activity compared with the pre-immunization value.

Cross-Protection Based on Inhibition of LPS-Induced IL-6 Secretion by Murine Peritoneal Macroshages Several monokines including tumor necrosis factor (TNF), IL-1, and IL-6 mediate many of the pathophysiologic events associated with Gram-negative endotoxemia. These monokines are secreted by monocytes and macrophages both in vitro and in vivo, in response to LPS. Serum with protective anti-LPS antibodies block the LPS induced macrophage or monocyte stimulation as shown in the following assay. This type of assay can be done using established mouse cell lines (e.g. J774.2), established human cell lines (e.g. THP-1), freshly obtained mouse peritoneal cells (C3H/HeN), or freshly obtained human monocytes/macrophages. Following stimulation with LPS, the assay can test for TNF or IL-6 levels. The amount of any type of LPS (e.g. *E. coli* R1) used to stimulate the cells needs to be determined in preliminary experiments. Too little LPS results in inadequate stimulation and undetectable monokine levels in the control group whereas too much LPS can overwhelm even a large amount of protective antibody. Serum with protective antibodies results in a lower monokine level (for example, the TNF level), compared with serum controls following stimulation with LPS.

In one example, this assay was performed as in Delahooke D M et al. Infection and Immunity, 1995, p 840–46. This assay uses a human cell line (THP1) which secretes TNF following stimulation with LPS. In this assay, the serum after vaccination with complete core antigen demonstrated significant inhibition of TNF induction In another example, mouse peritoneal cells (C3H/HeN) are obtained by peritoneal lavage with 0.34 M sucrose in distilled water. Peritoneal cells are seeded at 5×10$^5$ cells/ml in 0.2 ml serum free medium (IMDM-ATL, Schreier and Tees, Immunological Methods, Vol. II, Acad. Press (1981) :263) and cultured for 4 hours at 37 degrees C. in the presence or absence of (1) LPS, e.g. LPS from *E. coli* R3(0.05 ng/ml) or *E. coli* O18 (0.05 ng/ml) or *S. minnesota* wild type smooth (0.05 ng/ml) or *S. minnesota* R60 (0.05 ng/ml); and (2) in the presence or absence of diluted or undiluted serum from rabbits immunized with varying immunogens, e.g. composition described in this invention or Rc J5 mutant of *E. coli* or Re mutant of *S. minnesota*. The supernatants are recovered and the amount of IL-6 present in the supernatants is then measured using the IL-6 dependent hybridoma cell-line B13.29 (Aarden et al., Eur. J. Immunol. 1987, 17, 1911) as follows:

B13.29 cells are seeded at 2.5×10$^4$ cells/ml in serum free medium and cultured for 72 hrs in the absence of IL-6 and in the presence or absence of culture supernatant. Aliquots of the cultures (200 μl/well) are distributed in flat bottomed microtiter plates. IL-6 concentration in the supernatants is calculated in relation to a standard curve of IL-6. The post-immune serum should cause reduced IL-6 secretion compared to the pre-immune serum.

Cross-Protection from Lethal Dose of Endotoxin

Another measure of the effectiveness of this invention is its ability to confer cross-protection against LPS. A mouse lethality model is used in which mice are immunized intraperitonealy on Day 0 with either the invention, appropriate controls, or immunogens described previously such as the Rc J5 mutant LPS of *Escherichia coli* and the Re mutant LPS of *Salmonella minnesota*. A second dose of antigen is administered on Day 7 and Day 14. Between days 19 and 21 endotoxin can be administered intravenously in a 95% lethal dose of a particular LPS to groups of six female C57BL/6 mice, 6–8 weeks old. Galactosamine (D-GalN) (800 mg/kg) is administered intraperitoneally at the time of the LPS. The minimum intravenous dose of LPS required to kill approximately 95% of the animals (LD$_{95}$) is determined in preliminary experiments. Survival is recorded up to 24 hours. Alternative methods can be used in this protocol without substantially changing its ability to demonstrate whether immunization with a particular immunogen results in protective antibodies. For example, other strains of mice can be suitable, the galactosamine dose can be modified, and the dosing schedule of vaccination can be altered so as to administer more doses. The experiment can also be performed by isolating serum from rabbits immunized with the experimental immunogen, and then administering the serum to mice prior to challenge with galactosamine and LPS. This method using passive immunization can be used to demonstrate the protective nature of serum.

Example 1

Liposomes containing *E. coli* K12 complete-core LPS were made according to method #2, above. Liposomes containing a cocktail of six complete-core LPS (*E. coli* R1–R4, K12, *S. minnesota* R60 Ra) were made according to the method described above.

Groups of three mature rabbits were immunized intramuscularly using a dose of 0.5 mg of antigen with Alum (as described earlier) on days 0, 14, and 56. On days 0, 14, 21, 56, and 63, blood was withdrawn and processed as described earlier.

Using the ELISA method described earlier, rabbits immunized with K12 demonstrated increases in both IgM and IgG antibody levels to smooth and rough forms of LPS from *E. coli* and Salmonella bacteria.

Using the Western/immunoblot method described earlier, serum from both groups of immunized rabbits demonstrated enhanced binding to smooth and rough forms of LPS from *E. coli* and *Salmonella typhimurium*. Binding of serum from rabbits immunized to K12 alone to smooth forms of LPS from *E. coli* (serotypes 018, 012 and 015) as well as to the LPS from *Salmonella typhimurium* wild type was comparable to binding of serum from rabbits immunized with the cocktail of six complete LPS cores.

EXAMPLE 2

Purified lipopolysaccharide in equivalent amounts from the following rough strains of bacteria having a complete core, R1, R2, R3, R4, and K12 strains of Ra *E. coli* and the Ra strain of *Salmonella minnesota* R60, are tested either alone or following their incorporation into liposomes as described earlier. Heat killed cells and liposomes alone are also evaluated. Compositions are made according to the materials and methods described earlier.

Groups
1. 100 μg of MLV (no LPS)
2. Purified LPS (3 ng total) from *E. coli* R1
3. purified LPS (0.3 ng total) (0.05 ng each of *E. coli* K12,R1,R2,R3, and R4, and *S. minnesota* R60)
4. purified LPS (3 ng total) (0.5 ng each of *E. coli* K12,R1, R2,R3, and R4, and *S. minnesota* R60)
5. purified LPS (30 ng total) (5 ng each of *E. coli* K12,R1, R2,R3, and R4, and *S. minnesota* R60
6. purified LPS (300 ng total) (50 ng each of *E. coli* K12,R1,R2,R3, and R4, and *S. minnesota* R60)
7. Cocktail of the 6 LPSs mentioned above incorporated into MLVs as 1:1000 ratio by weight (LPS:lipid) (3 ng total) (0.5 ng each of *E. coli* K12,R1,R2,R3, and R4, and *S. minnesota* R60)
8. Cocktail of the 6 LPSs mentioned above incorporated into MLVs as 1:1000 ratio by weight (LPS:lipid) (30 ng total) (5 ng each of *E. coli* K12,R1,R2,R3, and R4, and *S. minnesota* R60)
9. Cocktail of the 6 LPSs mentioned above incorporated into MLVs as 1:1000 ratio by weight (LPS:lipid) (300 ng total) (50 ng each of *E. coli* K12,R1,R2,R3, and R4, and *S. minnesota* R60)
10. Cocktail of the 6 LPSs mentioned above incorporated into LUVs as 1:1000 ratio by weight (LPS:lipid) (3 ng total) (0.5 ng each of *E. coli* K12,R1,R2,R3, and R4, and *S. minnesota* R60)
11. Cocktail of the 6 LPSs mentioned above incorporated into LUVs as 1:1000 ratio by weight (LPS:lipid) (30 ng total) (5 ng each of *E. coli* K12,R1,R2,R3, and R4, and *S. minnesota* R60)
12. Cocktail of the 6 LPSs mentioned above incorporated into LUVs as 1:1000 ratio by weight (LPS:lipid) (300 ng total) (50 ng each of *E. coli* K12,R1,R2,R3, and R4, and *S. minnesota* R60)
13. Heat killed cells from *E. coli* R1 (amount that has same LAL activity as 3 ng of *E. coli* R1 LPS)

What is claimed is:

1. A method of reducing adverse effects of endotoxin in a warm-blooded animal, which comprises administering to the warm-blooded animal an effective amount of a composition comprising rough, complete-core lipopolysaccharide (LPS) antigens of at least two Gram negative bacterial strains, each of said strains having a classification independently selected from the following classifications: *E. coli*; Pseudomonas; and Bacteroides, said antigens being separated from cells of said bacterial strains.

2. The method of claim 1 in which the composition comprises Ra LPS incorporated in a liposome.

3. The method of claim 2 in which the composition comprises *E. coli* K12Ra LPS in a liposome.

4. The method of claim 2 in which the composition comprises a cocktail of Ra LPSs from multiple species of Gram-negative bacteria incorporated in liposomes.

5. The method of claim 1 or claim 4 in which the cocktail comprises Ra LPSs from at least three strains of Gram-negative bacteria, each of said strains being classified in a different one of the following classifications: *E. coli* K12, *E. coli* R1, *Bacteroides fragilis*, and *Pseudomonas aeruginosa*.

6. The method of claim 1 in which one of said bacterial strains is classified as *E. coli* K12.

7. The method of claim 6 in which the animal is a mammal.

8. The method of claim 7 in which the animal is a human patient.

9. The method of claim 6 in which the composition comprises LPS of an Ra rough *E. coli* K12.

10. The method of claim 1 in which both of said at least two bacterial strains are classified as *E. coli*.

11. The method of claim 1 or claim 6 in which the composition comprises complete-core, rough, LPS antigen from a third Gram-negative bacterial strain different from the first and from the second Gram-negative bacterial strains.

12. The method of claim 11 in which the composition comprises complete-core, rough, LPS antigen from a fourth Gram-negative bacterial strain different from each of the first, the second, and the third Gram-negative bacterial strains.

13. The method of claim 6 in which the other of said Gram-negative bacterial strains is *E. coli* R1.

14. The method of claim 12 in which complete core antigen from each of the four bacterial strains is present in generally equal amounts by weight.

15. The method of claim 11 in which the composition comprises LPS antigens from at least two different Gram-negative bacterial strains of the same species.

16. The method of claim 6 in which the antigens cause the patient to produce an antibody that binds to an epitope in the core region of the LPS of at least one Gram-negative bacterial strain whose LPS is not part of the composition.

17. The method of claim 16 in which the patient's antibody binds to the LPS of at least one smooth Gram negative bacterial strain.

18. The method of claim 2 in which the ratio (weight:weight) of lipid in the liposome to the LPS antigens is between 1:1 and 5000:1.

19. The method of claim 2 in which the ratio (weight:weight) is between 10:1 and 1000:1.

20. The method of claim 2 in which the liposome comprises a component selected from the group consisting of: phospholipid, cholesterol, positively charged compounds, negatively charged compounds, and amphipathic compounds.

21. The method of claim 2 in which the liposome is a multilamellar type liposome (MLV).

22. The method of claim 2 in which LPS in the acid salt form is incorporated into the liposome.

23. The method of claim 2 in which the liposome is a small or large unilamellar liposome (SUVs and LUVs).

24. The method of claim 1 in which the composition is administered intramuscularly, intravenously, subcutaneously, intraperitonealy, via the respiratory tract, or via the gastrointestinal tract.

25. The method of claim 1 in which the dose of antigen is over 0.01 ng per kilogram of patient body weight.

26. The method of claim 25 in which the dose is less than 1000 ng per kilogram of patient body weight.

27. The method of claim 25 in which the dose is less than 100 micrograms per kilogram of patient body weight.

28. The method of claim 1 in which the composition is administered in multiple doses, the first of which is administered at least 2 days prior to potential endotoxin exposure.

29. The method of claim 1 in which the composition further comprises an adjuvant.

30. The method of claim 29 in which the adjuvant is alum.

31. A method of reducing adverse effects of endotoxin in a warm-blooded animal, which method comprises administering to the warm-blooded animal an effective amount of antibody produced by immunization with a composition according to claim 1 or claim 6.

32. The method of claim 31 in which the antibody comprises a substantial percentage of IgM antibody.

* * * * *